(12) United States Patent
Uesugi et al.

(10) Patent No.: US 7,722,559 B2
(45) Date of Patent: May 25, 2010

(54) METHOD AND APPARATUS FOR SUPPLYING PREDETERMINED GAS INTO BODY CAVITIES OF A PATIENT

(75) Inventors: Takefumi Uesugi, Tokyo (JP); Daisuke Sano, Tokyo (JP); Atsuhiko Kasahi, Yokohama (JP); Kenji Noda, Tokyo (JP)

(73) Assignee: Olympus Corporation (JP)

( * ) Notice: Subject to any disclaimer, the term of this patent is extended or adjusted under 35 U.S.C. 154(b) by 997 days.

(21) Appl. No.: 11/093,389

(22) Filed: Mar. 30, 2005

(65) Prior Publication Data

US 2005/0234391 A1 Oct. 20, 2005

(30) Foreign Application Priority Data

Mar. 31, 2004 (JP) ............... 2004-108364

(51) Int. Cl.
*A61M 37/00* (2006.01)
(52) U.S. Cl. ............... 604/26; 600/560; 604/23; 604/24; 604/25; 604/28; 604/30; 604/31
(58) Field of Classification Search ............... 600/560; 604/23–26, 28, 30, 31
See application file for complete search history.

(56) References Cited

U.S. PATENT DOCUMENTS

| | | | |
|---|---|---|---|
| 3,858,572 A | 1/1975 | Binard et al. ............... 128/2 A |
| 4,595,004 A * | 6/1986 | Czech ............... 128/204.21 |
| 4,657,160 A * | 4/1987 | Woods et al. ............... 222/94 |
| 4,676,774 A * | 6/1987 | Semm et al. ............... 604/26 |
| 4,735,603 A | 4/1988 | Goodson et al. ............... 604/21 |
| 4,795,424 A | 1/1989 | Burner ............... 604/30 |
| 5,006,109 A * | 4/1991 | Douglas et al. ............... 604/26 |
| 5,013,294 A * | 5/1991 | Baier ............... 604/26 |
| 5,152,745 A | 10/1992 | Steiner et al. ............... 604/26 |
| 5,246,419 A * | 9/1993 | Absten ............... 604/26 |
| 5,328,458 A * | 7/1994 | Sekino et al. ............... 604/26 |
| 5,439,441 A * | 8/1995 | Grimsley et al. ............... 604/26 |
| 5,549,546 A * | 8/1996 | Schneider et al. ............... 604/23 |
| 5,590,684 A * | 1/1997 | Alberts et al. ............... 137/489 |
| 5,676,650 A | 10/1997 | Grieshaber et al. ............... 604/28 |
| 5,830,176 A * | 11/1998 | Mackool ............... 604/22 |
| 5,979,488 A * | 11/1999 | Smith et al. ............... 137/312 |
| 6,126,610 A | 10/2000 | Rich et al. ............... 600/529 |
| 6,206,878 B1 | 3/2001 | Bishop et al. ............... 606/49 |
| 6,299,592 B1 | 10/2001 | Zander ............... 604/26 |

FOREIGN PATENT DOCUMENTS

| | | |
|---|---|---|
| JP | 08-256972 | 10/1996 |
| JP | 2000-139823 | 5/2000 |
| JP | 2000-139830 | 5/2000 |

* cited by examiner

*Primary Examiner*—Nicholas D Lucchesi
*Assistant Examiner*—Scott Medway
(74) *Attorney, Agent, or Firm*—Ostrolenk Faber LLP

(57) ABSTRACT

A gas supply apparatus measures a first pressure inside a first body cavity of a specimen and a second pressure inside a second body cavity of the specimen. The gas supply apparatus regulates a pressure of a predetermined gas based on the measured first and second pressures inside the first and second body cavities so that the first and second pressures reach predetermined first and second pressure settings, respectively.

13 Claims, 14 Drawing Sheets

METHOD AND APPARATUS FOR SUPPLYING PREDETERMINED GAS INTO BODY CAVITIES OF A PATIENT

CROSS REFERENCE TO RELATED APPLICATION

This application is based upon the prior Japanese Patent Application 2004-108364 filed on Mar. 31, 2004 and claims the benefit of priority therefrom so that the descriptions of which are all incorporated herein by reference.

BACKGROUND OF THE INVENTION

1. Field of the Invention

The present invention relates to a method and a system for supplying predetermined gas into body cavities of a specimen.

2. Description of the Related Art

In recent years, laparoscopic surgeries have been practiced extensively. The laparoscopic surgery is executed for treating a patient with minimally invasive capability.

Specifically, in the laparoscopic surgeries, for example, a first trocar for introducing a rigid endoscope, referred to as "rigidscope", for observation to a body cavity of a patient is inserted thereinto. In addition, a second trocar for introducing a treatment tool to a site to be treated is inserted thereinto.

In such a laparoscopic surgery, an insufflator has been used for supplying carbon dioxide gas (hereinafter also referred to as $CO_2$) as insufflating gas into an abdominal cavity of the patient to ensure the rigidscope field and a space to manipulate the treatment tool.

Conventionally, some types of insufflators each for supplying carbon dioxide into one of body cavities, such as an abdominal cavity of the patient, have been prepared.

For example, Japanese Unexamined Patent Publication No. 2000-139830 discloses a gas supplying apparatus designed to feed a control signal to a pressure-regulating valve when gas flow volume does not reach a predetermined value. The control signal causes the pressure-regulating valve to increase the pressure of the output gas to control the amount thereof, thereby keeping an internal pressure of a living body at the predetermined value.

Moreover, Japanese Unexamined Patent Publication No. 8-256972 discloses an insufflator having a plurality of electro magnetic valves for controlling a state of gas flowing through a gas delivery channel extending from a gas supply source to an insufflation tool. Specifically, the insufflator is designed so that the plurality of electro magnetic values is integrated with a manifold valve, allowing the gas-flow state controlling section to become compact.

Furthermore, Japanese Unexamined Patent Publication No. 2000-139823 discloses an insufflation system for insufflating air into a lumen to keep constant the pressure inside of the lumen.

In the meanwhile, when diagnosing and treating a lumen, such as the stomach, the large intestine, or the like of a patient as one of the body cavities thereof, a flexible endoscope, referred to as "flexiblescope", and a treatment tool therefore have been used. The flexiblescope has one thin and flexible end portion to be used as an access site into the lumen. The treatment tool for the flexiblescope is designed so that its forceps channel is inserted into the flexiblescope to project through an opening formed in the head of the one end portion of the flexiblescope.

When executing curative intervention, such as diagnosis and treatment of a lumen, such as the stomach, the large intestine or the like of a patient under such monitored conditions with the flexiblescope, in some cases, gas for lumens is injected into the lumen. The injection of gas aims at securing the flexiblescope field and a space to manipulate the treatment tool.

In these cases, the gas to be supplied into the lumen can be transferred with a gas supply pump. As the gas for lumens, air has been generally applied, but the carbon dioxide gas can be used Recently, as a new attempt, in the laparoscopic surgeries, the rigidscope is inserted into an abdominal cavity of a patient with the flexiblescope inserted into a lumen of the patient. This allows identification of a site to be treated in the patient based on an image of the inside of the abdominal cavity, which is obtained by the rigidscope, and that of the inside of the lumen, which is obtained by the flexiblescope.

Under such monitored conditions with both the rigidscope and flexiblescope, in some cases, for example, air as gas for lumens is injected through the flexiblescope into the lumen so that the lumen inflates.

When air is supplied into the lumen, it is difficult for the air to be absorbed into the living body. This may cause the lumen to remain inflated.

For this reason, when inserting the rigidscope into an abdominal cavity of a patient while inserting the flexiblescope into a lumen thereof, using an endoscope $CO_2$ regulator (hereinafter referred to as ECR) has been considered to supply carbon dioxide gas ($CO_2$), which is absorbed easily into the living body, into the lumen.

SUMMARY OF THE INVENTION

The present invention has been made on the background.

According to one aspect of the present invention, there is provided a gas supply apparatus for supplying predetermined gas to a first body cavity of a specimen through a first delivery member and to a second body cavity of the specimen through a second delivery member. The gas supply apparatus has a pressure regulator coupled to the first and second delivery members and configured to regulate a pressure of the predetermined gas. The gas supply apparatus has a pressure measuring unit configured to individually measure a first pressure inside the first body cavity and a second pressure inside the second body cavity. The gas supply apparatus has a controller electrically connected to the pressure regulator and the pressure measuring unit and operative to control the pressure regulator based on the measured first and second pressures inside the first and second body cavities so that the first and second pressures reach predetermined first and second pressure settings, respectively.

According to another aspect of the present invention, there is provided a gas insufflating apparatus for insufflating predetermined gas to a first body cavity of a specimen through a first delivery member and to a second body cavity of the specimen through a second delivery member. The gas insufflating apparatus has means for measuring a first pressure inside the first body cavity and a second pressure inside the second body cavity. The gas insufflating apparatus has means for regulating a pressure of the predetermined gas based on the measured first and second pressures inside the first and second body cavities so that the first and second pressures reach predetermined first and second pressure settings, respectively.

According to a further aspect of the present invention, there is provided an observation system has a gas supply apparatus for supplying predetermined gas to a first body cavity of a specimen through a first delivery member and to a second body cavity of the specimen through a second delivery member. The gas supply apparatus is provided with a pressure regulator coupled to the first and second delivery members and configured to regulate a pressure of the predetermined gas. The gas supply apparatus is provided with a pressure measuring unit configured to measure a first pressure inside the first body cavity and a second pressure inside the second body cavity. The gas supply apparatus is provided with a controller electrically connected to the pressure regulator and the pressure measuring unit and operative to control the pressure regulator based on the measured first and second pressures inside the first and second body cavities so that the first and second pressures reach predetermined first and second pressure settings, respectively. The observation system has an observation device integrated with a gas delivery channel and configured to be inserted into the second body cavity of the specimen to observe an inside of the second body cavity. The gas delivery channel serves as part of the second delivery member.

According to a still further aspect of the present invention, there is provided a method of insufflating predetermined gas to a first body cavity of a specimen through a first delivery member and to a second body cavity of the specimen through a second delivery member. The method includes measuring a first pressure inside the first body cavity and a second pressure inside the second body cavity. The method includes regulating a pressure of the predetermined gas based on the measured first and second pressures inside the first and second body cavities so that the first and second pressures reach predetermined first and second pressure settings, respectively.

BRIEF DESCRIPTION OF THE DRAWINGS

Various aspects of the present invention will be more particularly described with reference to the accompanying drawings in which.

DETAILED DESCRIPTION OF EMBODIMENTS OF THE INVENTION

Embodiments of the present invention will be described hereinafter with reference to the accompanying drawings.

First Embodiment

Figure 1:
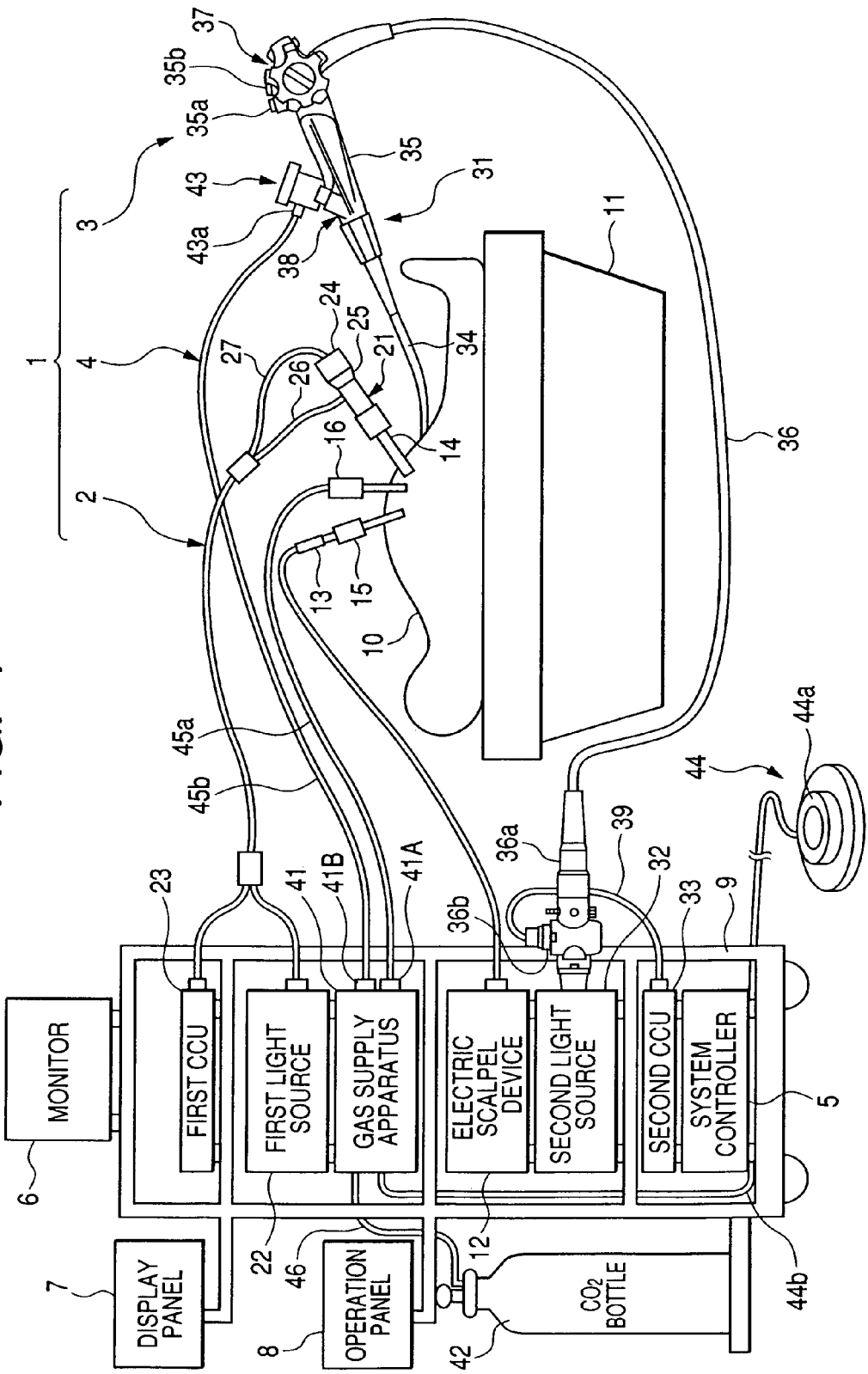
FIG. 1 is an overall structural view schematically illustrating the structure of an endoscopic surgical system equipped with a gas supply apparatus according to a first embodiment of the present invention.

As shown in FIG. 1, a laparoscopic surgery system, referred to as a surgical system hereinafter, 1 has a first endoscope system 2, a second endoscope system 3, and a gas supply system 4 according to an embodiment of the present invention.

The surgical system 1 has a system controller 5, a monitor 6 as a display device, a center display panel 7, a center operation panel 8, and a movable cart (trolley) 9.

Reference numeral 10 designates a patient as a specimen, and reference numeral 11 designates an operation table that allows the patient 11 to lie thereon. Reference numeral 12 designates an electric scalpel device as an example of operation devices, which is mounted on the cart 9. The surgical system 1 has an electric scalpel 13 serving as an operation tool. The electric scalpel 13 is electrically connected to the electric scalpel device 12.

Reference numerals 14, 15, and 16 designate first, second, and third trocars, which are inserted into, for example, an abdominal portion of the patient 10, respectively. The first trocar 14 allows an endoscope, described herein after, of the first endoscope system 2 to be guided into a first body cavity, such as an abdominal cavity AC (see FIG. 2) of the patient 10. The abdominal cavity AC, which means a cavity separated by the diaphragm from the thoracic cavity above and by the plane of the pelvic inlet from the pelvic cavity below, serves as a first body cavity of the patient 10 according to the first embodiment.

The second trocar 15 permits guide of a treatment tool into the abdominal cavity AC. The treatment tool, such as the electric scalpel 13, is operative to remove and/or treat a tissue corresponding to at least one site to be treated in the abdominal cavity AC.

The third trocar 16 allows gas for the abdominal cavity, such as carbon dioxide gas, to be introduced into the abdominal cavity AC. The carbon dioxide gas, referred to as "$CO_2$" can be easily absorbed into a living body, such as the patient 10, which is supplied from the gas supply system 4. The carbon dioxide gas can be introduced into the inside of the abdominal cavity AC through at least one of the trocars 14 and 15.

The first endoscope system 2 includes a rigid endoscope 21 as a first endoscope with, for example, a rigid insert portion at one end thereof. The rigid endoscope 21 is referred to as "rigidscope" hereinafter. The first endoscope system 2 includes a first light source 22, a first camera control unit, referred to as "first CCU" hereinafter, and a camera (TV camera) for endoscopes. The first endoscope system 2 includes a camera for endoscopes.

One end portion of the insertion portion (not shown) of the rigidscope 21, for example, is configured to be inserted in part into the first trocar 14. The rigidscope 21 is provided with an illumination optics (not shown) and an observation optics (not shown), which are installed in the one end portion of the insertion portion. The illumination optics is composed of, for example, a light guide and the like, and configured to illuminate light onto a target, such as the site to be treated, of the inside of the patient 10. For example, the observation optics is composed of relay lenses and the like. The observation optics is configured to optically deliver an optical image of the target illuminated by the light.

The rigidscope 21 is provided at the other end side of the insertion portion with an eyepiece 25 that allows an operator to observe the optical image delivered by the observation optics. The camera 24 is detachably installed in the eyepiece 25. The camera 24 is integrated with an image pickup device, such as a CCD (Charge Coupled Device) or the like, having a light sensitive pixel area, wherein the optical image delivered by the observation optics is focused on the light sensitive pixel area thereof. The optical image of the target focused on the light sensitive pixel area of the image pickup device is photoelectrically converted into an electric signal as a first image signal, by the image pickup device.

The first endoscope system 2 is provided with a light guide cable 26 extending from one side of the other end of the rigidscope 21. The light guide cable 26 is optically coupled to the first light source 22, allowing optical coupling between the rigidscope 21 and the first light source 22. The first endoscope system 2 is provided with an image pickup cable 27 electrically connecting between the first CCU 23 and the camera 24.

The first light source 22 has a function of supplying illumination light to the illumination optics of the rigidscope 21 via the light guide cable 26. The first CCU 23 is operative to execute electrical drive control of the image pickup device of the camera 24. When the first image signal corresponding to the optical image of the target, which is picked up by the image pickup device, is sent to the first CCU 23, the first CCU 23 is operative to receive the first image signal to subject the received first image signal to image processing of necessity. The first CCU 23 is operative to output the image-processed first image signal to at least one of the monitor 6 and the center display panel 7.

These operations allow at least one of the monitor 6 and the center display panel 7 to display a first image of the target thereon based on the first image signal. That is, the first image is an endoscopic image corresponding to the first image signal picked up by the rigidscope 21.

The second endoscope system 3 includes a flexible endoscope 31 as a second endoscope with, for example, a flexible insert portion 34 at one end thereof. The flexible insert portion is so flexible that it can be inserted into a lumen BC as a second body cavity of the patient. In the specification, the lumen is defined as the cavity of an organ in a specimen, such as the cavity of the stomach, the cavity of the large intestine, the cavity of a blood vessel, or the like in the specimen. The flexible endoscope 31 is referred to as "flexiblescope" hereinafter. The second endoscope system 3 includes a second light source 32, and a second CCU 33.

The flexiblescope 31 has a substantially hollow-rod (tubular) shape, which is narrow in diameter and flexible. The flexiblescope 31 is internally formed with a gas delivery channel SC (see FIG. 5).

Specifically, the flexiblescope 31 is provided at its one end with the insert portion 34 to be inserted at its one end into the interior of the lumen BC, and a manipulator 35 whose one end is joined to the other end of the insert portion 34. The manipulator 35 allows, for example, an operator to manipulate the flexiblescope 31. The flexiblescope 31 is provided with a universal cord 36 whose one end is joined to the other end of the manipulator 35.

The manipulator 35 is provided with a gas and water supply switch 35a mounted thereon. The gas and water supply switch 35a is formed with a through hole, also referred to as "gas and water supply channel), communicated with the gas delivery channel SC inside of the manipulator 35. The gas and water supply switch 35a, the gas delivery channel SC, and the insert portion 34 allow the operator to supply gas and water therethrough.

It should be noted that the term "operator" through the specification is not necessarily limited to a person who actually treats; the term "operator" refers to a concept that involves any of nurses or other operators who assist such a treatment action.

The manipulator 35 is provided with a suction switch 35b disposed thereto and a flexion knob 35c that allows the operator to flex a flexible portion (not shown) of the flexiblescope 31. The manipulator 35 is formed with a treatment tool channel 34a communicated with the gas delivery channel SC, and the flexiblescope 31 is provided with a treatment tool insertion opening 38 formed to be communicated with the treatment tool channel 34a in the manipulator 35. The treatment tool insertion opening 38 allows treatment tools to be inserted therethrough. The other end of the universal cord 36 is coupled to a light source connector 36a optically detachably so that the universal cord 36 is optically coupled to the second light source 32 through the light source connector 36a.

In the first embodiment, for example, the treatment tool channel 34a is larger than the gas and water supply channel in inner diameter, and is shorter than the gas and water supply channel in axial length.

The second light source 32 has a light source and an optical system (that are not shown) so that illumination light supplied from the second light source 32 is transferred to the flexiblescope 31 through the light source connector 36a and the universal cord 36.

The flexiblescope 31 is provided at its one end of the insertion portion 34 with an illumination optics. The illumination optics is composed of a light guide that can illuminate light on a target inside the patient 10, such as the lumen BC, through an illumination window disposed to one side of the one end of the insertion portion 34.

The flexiblescope 31 is provided with an image pickup device, such as a CCD (Charge Coupled Device) or the like, installed in the one end of the insertion portion 34. The image pickup device has a light sensitive pixel area. The image pickup device is so arranged that an optical image of the target illuminated by the light outputted from the illumination optics is focused on the light sensitive pixel area of the image pickup device.

The image pickup device of the flexiblescope 31 is electrically connected to the second CCU 33 through the universal cord 36 and the like. Reference numeral 39 is an electric cable electrically connecting between an electric connector 36b attached to the light source connector 36a and the second CCU 33.

The image pickup device is operative to photoelectrically convert the optical image of the target focused on the light sensitive pixel area into an electric signal as a second image signal.

The second CCU 33 is operative to execute electrical drive control of the image pickup device. When the second image signal corresponding to the optical image of the target, which is picked up by the image pickup device, is sent to the second CCU 33 through the electric cable 39, the second CCU 33 is operative to receive the second image signal to subject the received first image signal to image processing of necessity. The second CCU 33 is operative to output the image-processed second image signal to at least one of the monitor 6 and the center display panel 7.

These operations allow at least one of the monitor 6 and the center display panel 7 to display a second image of the target thereon based on the second image signal. That is, the second image is an endoscopic image corresponding to the second image signal picked up by the flexiblescope 31.

Turning now to the gas supply system 4, it includes a gas supply apparatus 41, a carbon dioxide gas cylinder ($CO_2$ bottle) 42 as a supplier, and an insertion adapter, referred to simply as adapter, 43. The gas supply system 4 has a foot switch 44 serving as an operation switch for controlling supply of the carbon dioxide gas into the lumen BC, an abdominal cavity tube 45a, and a lumen tube 45b. The $CO_2$ bottle 42 stores carbon dioxide in liquid.

The gas supply apparatus 41 is provided with a first adapter (connector) 41A for insufflation into the abdominal cavity AC and a second adapter 41B for insufflation into the lumen BC. The first adapter 41A is airtightly coupled to one end of the abdominal cavity tube 45a. The other end of the abdominal cavity tube 45a is airtightly coupled to the third trocar 16. The second adapter 41B is airtightly coupled to one end of the lumen tube 45b. The other end of the lumen tube 45b is airtightly coupled to a tube coupler 43a formed on one side of the adapter 43, which allows the lumen tube 45b to be communicated with the gas delivery channel SC inside the flexiblescope 31 through the adapter 43.

The foot switch 44 is provided with a switch portion 44a and is configured to provide instructions to instruct supply of the carbon dioxide gas into the lumen BC to the gas supply apparatus 41 while the operator or the like depresses the switch portion 44a with operator's foot or the like.

The gas supply apparatus 41 and the $CO_2$ bottle 42 is coupled to each other through a high-pressure gas tube 46. The gas supply apparatus 41 and the foot switch 44 are electrically connected to each other through a foot switch cable 44b. The electrical connection between the foot switch 44 and the gas supply apparatus 41 can be established by wireless. Each of the tubes 45a and 45b is made of a material such as, for instance, silicone, Teflon®, or other similar materials.

The system controller 5 is operative to perform control of the whole system 1. With the system controller 5, the center display panel 7, the center operation panel 8, and peripheral devices including the electric scalpel device 12, the first light source 22, the second light source 32, the first CCU 23, the second CCU 33, and the gas supply apparatus 41 are communicably connected through communication buses (not shown), respectively.

The monitor 6 has a function of receiving the first and second image signals outputted from the first and second CCUs 23 and 33 to display at least one of the first and second images thereon based on the received first and second image signals.

The center display panel 7 is composed of a display screen, such as a liquid crystal screen or the like. The center display panel 7 allows concentrative display of operating states of the peripheral devices together with the first and second images on the display screen.

The center operation panel 8 is designed to a touch panel and composed of a display section, such as a liquid crystal screen or the like, and a touch-sensitive device integrally formed on the display screen. The display section of the center operation panel 8 has a display function of providing a setting screen on which operable switches (buttons) for the peripheral devices are graphically displayed. The display section has an operating function of operating the operable switches by touching them. The center operation panel 8 is electrically connected to the system controller 5.

Specifically, the operator touches at least one of the operable switches with, for example, a finger so that the touch-sensitive device sets operating conditions corresponding to at least one of the touched operable switches to remotely send to the system controller 5 instructions for operating a corresponding one of the peripheral devices based on the set operating conditions. These remote operations of the graphical operable switches on the center operation panel 8 with respect to the peripheral devices are substantially identical to direct operations of operable switches directly attached to the peripheral devices.

The peripheral devices including the electric scalpel device 12, the first and second light sources 22 and 32, the first and second CCUs 23 and 33, the gas supply apparatus 41, and a VTR (Video Tape Recorder), which is not shown, are mounted on the cart 9. In addition, the system controller 5, the center display panel 7, and the center operation panel 8 are mounted on the cart 9.

Figure 2:
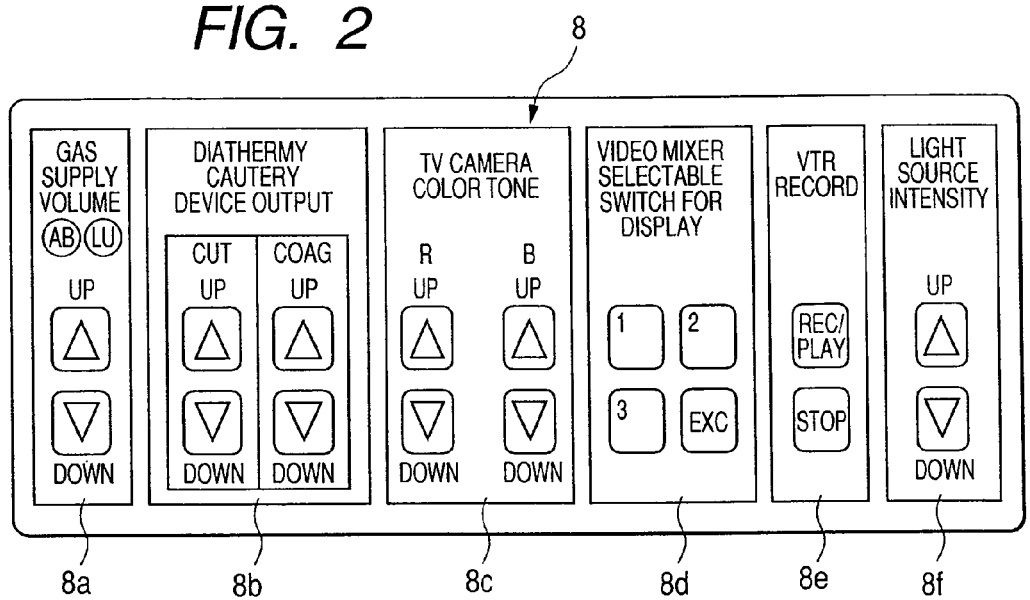
FIG. 2 is a view schematically illustrating a configuration example of an operation panel illustrated in FIG. 1.

A configuration example of the operation panel 8 is illustrated in FIG. 2.

The operation panel 8 is composed of a display screen, such as a liquid crystal display, and a touch-sensitive device integrally formed on the display screen. On the display screen, manually operable sections, such as manually operable graphical buttons, are displayed. The manually operable sections allow the operator to set operating conditions (parameters) with respect to the peripheral devices to give instructions for operating them based on the set operating conditions to the system controller 5 or the corresponding peripheral device.

Specifically, the operator touches at least one of the operable sections (operable buttons), with, for example, a finger so that the touch-sensitive device sets operating conditions corresponding to at least one of the touched operable sections to send to the system controller 5 instructions for operating the corresponding one of the peripheral devices based on the set operating conditions. The system controller 5 controls the corresponding one of the peripheral devices based on the instructions so that the corresponding one of the peripheral devices operates under the set operating conditions.

For example, as shown in FIG. 2, manual operation buttons 8a are graphically displayed on the display screen of the operation panel 8. The manual operation buttons 8a allow the operator to adjust the flow-rate of carbon dioxide gas supplied to the abdominal cavity AC or the lumen BC from the gas supply apparatus 41.

Manual operation buttons 8b are graphically displayed on the display screen of the operation panel 8. The manual operation buttons 8b permit the operator to adjust an output value of the electric scalpel device 12. Manual operation buttons 8c are graphically displayed on the display screen of the operation panel 8. The manual operation buttons 8c allow the operator to control color tones of the first and second CCUs 23 and 33.

In addition, manual operation buttons 8d are graphically displayed on the display screen of the operation panel 8. The manual operation buttons 8d allow the operator to send instructions to the system controller 5 for selectively switching the first image (the endoscopic image of the rigidscope 21) and the second image (the endoscope image of the flexiblescope 31), which are displayed on the monitor 6.

Manual operation buttons 8e are graphically displayed on the display screen of the operation panel 8. The manual operation buttons 8e allow the operator to send instructions to the system controller 5 for making the VTR start recording the first image and/or second image on a video tape or for stopping the record of the first image and/or second image thereon.

Manual operation buttons 8f are graphically displayed on the display screen of the operation panel 8. The manual operation buttons 8f permit the operator to adjust light intensity of the illumination light irradiated from the first light source 22 and that of the illumination light irradiated from the second light source 32.

Figure 3:
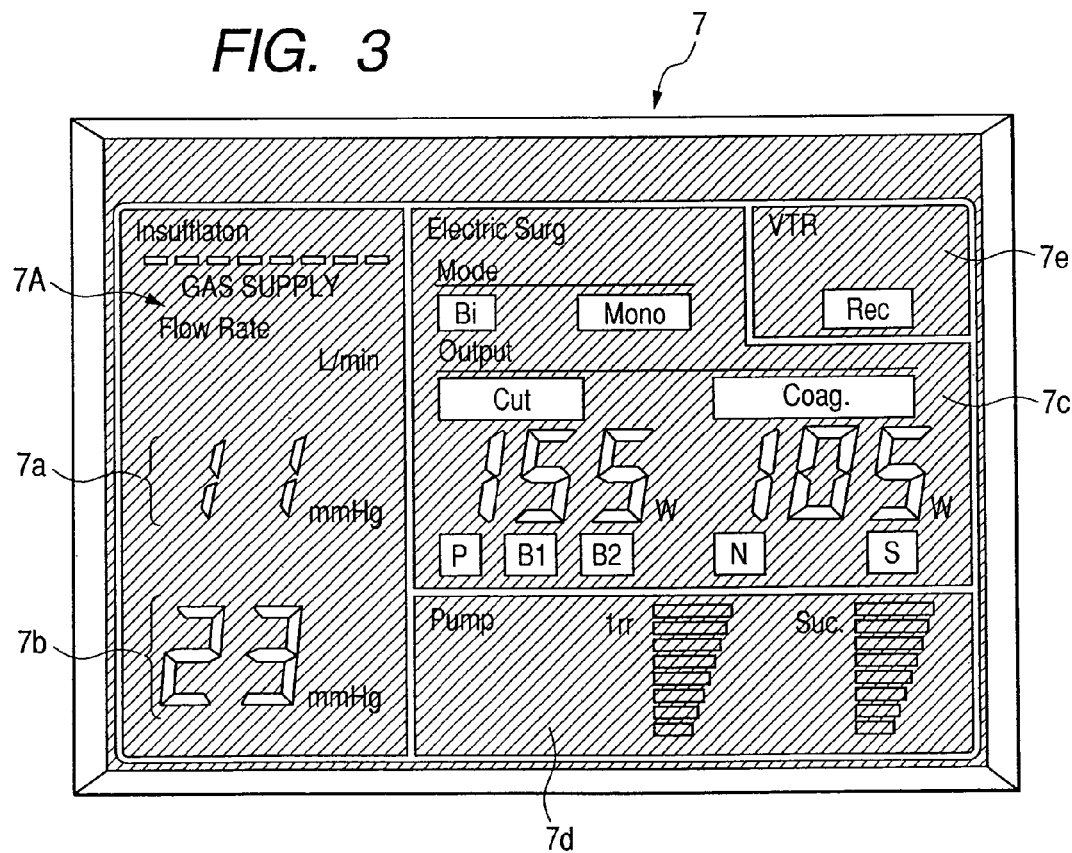
FIG. 3 is a view schematically illustrating an example of a display panel illustrated in FIG. 1.

An example of the display panel 7 shown in FIG. 1 is illustrated in FIG. 3.

As illustrated in FIG. 3, display areas 7A (7a, 7b), 7c, 7d, and 7e are graphically represented on the display screen of the display panel 7. The display areas 7A (7a, 7b), 7c, 7d, and 7e are allocated to the gas supply apparatus 41, the electric scalpel device 12, a water pump (not shown), and the VTR, which are communicated to be controlled by the system controller 5, respectively.

The current settings of the peripheral devices and the operating states thereof are displayed on the corresponding display areas 7A, (7a, 7b), 7c, 7d and 7e, respectively. For example, the display area 7A is operative to display the settings and the operating state of the gas supply apparatus 41. Specifically, the display area 7A includes a display area 7a on which a current pressure inside the lumen BC of the patient 10 is displayed, and a display area 7b on which a current pressure inside the abdominal cavity AC of the patient 10 is displayed. The display area 7A also includes display areas for displaying the flow-rate (FLOW RATE) of the carbon dioxide gas supplied from the gas supply apparatus 41 and the volume (GAS SUPPLY) of the carbon dioxide gas remaining in the $CO^2$ bottle 42.

Next, a configuration example of the manually operable setting section 63 and the display section 64 provided on a front panel FP of the gas supply apparatus 41 is described with reference to FIG. 4. In the first embodiment, for example, the front panel FP is attached along one side of a housing of the gas supply apparatus 41.

Figure 4:
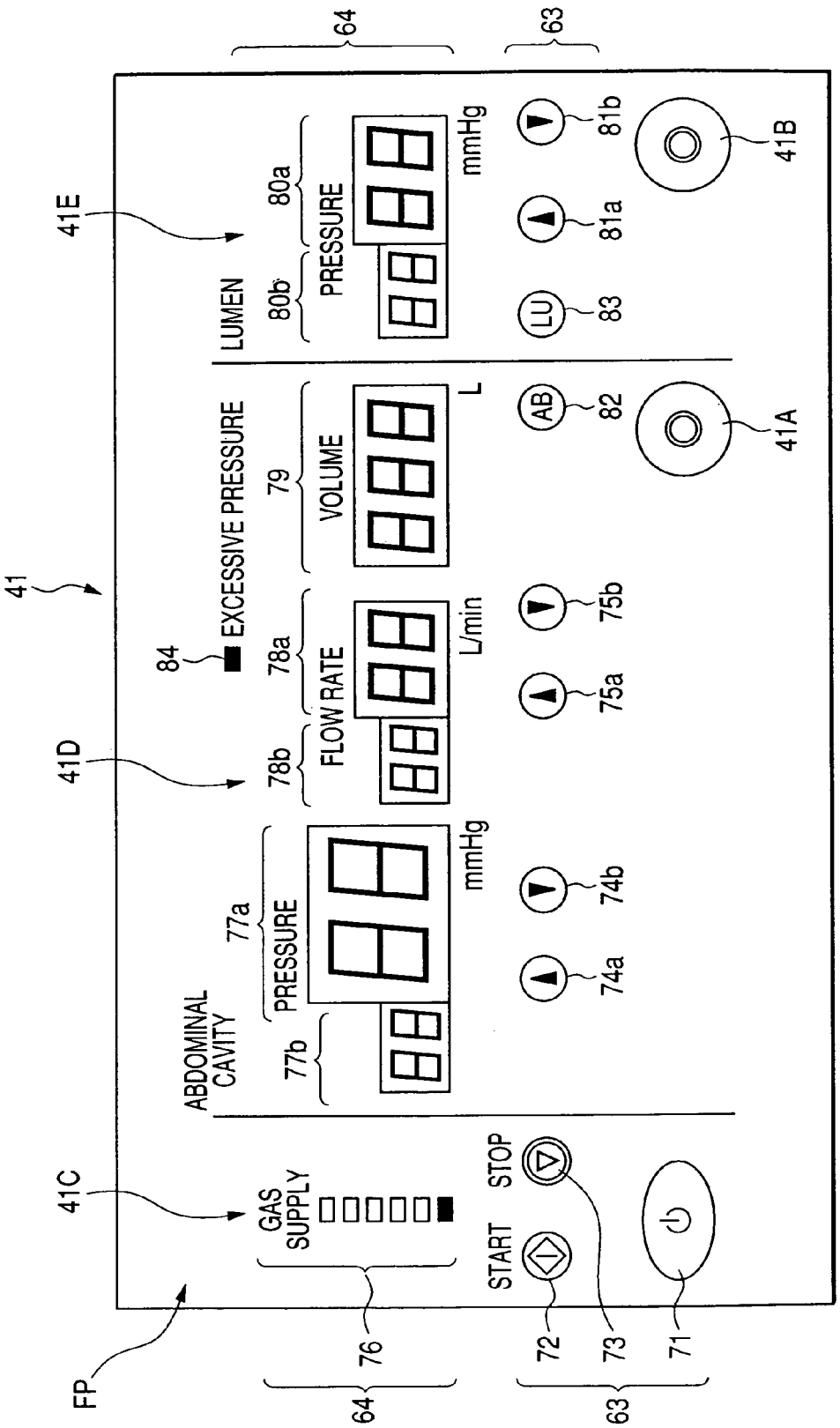
FIG. 4 is a view schematically illustrating a configuration example of a manually operable setting section and a display section provided on a front panel of the gas supply apparatus illustrated in FIG. 1.

As shown in FIG. 4, the manually operable setting section 63 and the display section 64 are graphically displayed on the front panel FP of the gas supply apparatus 41. The manually operable setting section 63 and display section 64 are divided in, for instance, three graphical setting and display sections 41C to 41E.

The setting and display section 41C serves as a supply source setting and display section that allows the operator to enter instructions related to the carbon dioxide gas supplied from the $CO_2$ bottle 42. In addition, the setting and display section 41C is designed to display the state of carbon dioxide gas supplied from the $CO_2$ bottle 42.

The setting and display section 41D serves as a setting and display section for an abdominal cavity. Specifically, the setting and display section 41D allows the operator to set parameters related to the pressure inside the abdominal cavity AC and the insufflation of carbon dioxide gas thereinto. The setting and display section 41D allows the operator to enter instructions related to the pressure inside the abdominal cavity AC and the insufflation of carbon dioxide gas thereinto. The setting and display section 41D is designed to display the state of the abdominal cavity AC depending on the carbon dioxide gas being insufflated thereinto.

The setting and display section 41E serves as a setting and display section for lumen BC. Specifically, the setting and display section 41E allows the operator to set parameters related to the insufflation of carbon dioxide gas into the lumen BC; the setting and display section 41E is designed to display the state of the lumen BC depending on the carbon dioxide gas being insufflated thereinto.

The first adaptor 41A is attached to the lower side of the setting and display section 41D of the front panel FP; the second adaptor 41B is attached to the lower side of the setting and display section 41E of the front panel FP.

The setting and display section 41C is provided with a power switch 71, a gas-supply start button 72, and a gas-supply stop button 73a as the manually operable setting section 63. In addition, the setting and display section 41C is provided with a gas remaining volume indicators 76 as the display section 64.

The setting and display section 41D is provided with pressure displays 77a and 77b for the pressure inside the abdominal cavity AC, flow-rate displays 78a and 78b for the abdominal cavity AC, a total volume display 79 for the abdominal cavity AC, and an excessive pressure indicator 84 for the abdominal cavity AC as the display section 64.

The setting and display section 41D is provided with pressure setting buttons 74a and 74b for the pressure inside the abdominal cavity AC, flow-rate setting buttons 75a and 75b for the abdominal cavity AC, and an abdominal cavity select button 82 (see "AB" in FIG. 4) as the manually operable setting section 63.

The setting and display section 41E is provided with pressure displays 80a and 80b for the lumen BC as the display section 64.

The setting and display section 41E is provided with pressure setting buttons 81a and 81b for the lumen BC and a lumen select button 83 (see "LU" in FIG. 4) as the manually operable setting section 63.

The power switch 71 serves as a switch that permits the operator to turn power on and off to the apparatus 41. The gas-supply start button 72 serves as a button that allows the operator to send an instruction to start the supply of the carbon dioxide gas into the abdominal cavity AC to a controller 98 described hereinafter. The gas-supply stop button 73 serves as a button that permits the operator to send an instruction to stop the supply of the carbon dioxide gas to the controller 98.

The pressure setting buttons 74a and 74b serve as buttons that allow the operator to send instructions to change the corresponding parameter (the pressure inside the abdominal cavity AC) to a pressure setting. The flow-rate setting buttons 75a and 75b serve as buttons that enable the operator to send instructions to change the corresponding parameter (the flow-rate of the carbon dioxide gas to be delivered into the abdominal cavity AC) to a flow-rate setting. The flow-rate setting buttons 81a and 81b serve as buttons that permit the operator to send instructions to change the corresponding parameter (the flow-rate of the carbon dioxide gas being delivered into the lumen BC) to a flow-rate setting.

Specifically, the pressure setting buttons include an up button 74a and a down button 74b. Every time the operator clicks the up button 74a, the pressure setting inside the abdominal cavity AC turns up; every time the operator clicks the down button 74b, the pressure setting turns down. The pressure setting variably determined by the up and down buttons 74a and 74b is sent to the controller 98 every time at least one of the up and down buttons 74a and 74b is operated.

Similarly, the flow-rate setting buttons include an up button 75a and a down button 75b. The flow-rate setting of the carbon dioxide gas to be insufflated into the abdominal cavity AC turns up every time the operator clicks the up button 75a; the flow-rate setting turns down every time the operator clicks the down button 75b. The flow-rate setting variably set by the up and down buttons 75a and 75b is sent to the controller 98 every time at least one of the up and down buttons 75a and 75b is operated.

Furthermore, the pressure setting buttons include an up button 81a and a down button 81b. The pressure setting of the carbon dioxide gas to be insufflated into the lumen BC turns up every time the operator clicks the up button 81a; the pressure setting turns down every time the operator clicks the down button 81b. The pressure setting variably set by the up and down buttons 81a and 81b is sent to the controller 98 every time at least one of the up and down buttons 81a and 81b is operated.

The gas remaining volume indicators 76 are vertically arranged so that a top indicator that is lighting indicates the amount of carbon dioxide gas available.

The right-side pressure display 77a is configured to display a pressure value (in mmHg) based on a measured value of a first pressure sensor 95A described hereinafter. The left-side pressure display 77b is configured to display the pressure setting determined based on the operations of, for example, the pressure setting buttons 74a and 74b.

The right-side flow-rate display 78a is configured to display a flow-rate (in L/min) based on a measured value of a first flow-rate sensor 96A described hereinafter. The left-side flow-rate display 78b is configured to display the flow-rate setting determined based on the operations of, for example, the flow-rate setting buttons 75a and 75b.

The total volume display 79 is configured to display a total amount of carbon dioxide gas calculated by the controller 98 based on the measured value of the first flow-rate sensor 96A.

The right-side pressure display 80a is configured to display a pressure (in mmHg) based on a measured value of a second pressure sensor 95B described hereinafter. The left-side pressure display 80b is configured to display the pressure setting determined based on the operations of, for example, the pressure setting buttons 81a and 81b.

When the operator turns on the abdominal cavity select button 82, the button 82 is configured to send to the controller 98 an instruction to make it execute operations for supplying the carbon dioxide gas into the abdominal cavity AC. In other words, when the operator turns on the abdominal cavity select button 82, the button 82 is configured to send to the controller 98 an instruction to change the operation mode thereof to an abdominal cavity insufflation mode.

When the operator turns on the lumen select button 83, the button 83 is configured to send to the controller 98 an instruction to make it execute operations for supplying the carbon dioxide gas into the lumen BC. In other words, when the operator turns on the lumen select button 83, the button 83 is configured to send to the controller 98 an instruction to change the operation mode thereof to a lumen insufflation mode.

The excessive pressure indicator 84 consists of, for example, red LED (light emitting device). The excessive pressure indicator 84 is configured to turn on or flash on and off based on a control signal sent from the controller 98 at anytime the pressure measured by the first pressure sensor 96A exceeds a threshold value of the pressure inside the abdominal cavity AC by a predetermined pressure. The turning-on or the flashing of the excessive pressure indicator 84 allows the operator to visually recognize that the pressure inside the abdominal cavity AC exceeds the threshold value by the predetermined pressure or more.

Incidentally, an excessive pressure indicator that is the same as the excessive pressure sensor 84 may be provided on the setting and display section 41E.

In addition, the center operation panel 8 allows the operator to set the parameters of the gas supply apparatus 41, which include the setting of the pressure inside the abdominal cavity AC, and the settings of the flow-rates for the abdominal cavity AC and the lumen BC. Specifically, the settings determined on the center operation panel 8 for the corresponding parameters are sent to the controller 98 through the system controller 5. The controller 98 carries out abdominal-cavity pressure control, lumen pressure control, abdominal-cavity flow-rate control, and lumen flow-rate control based on the corresponding parameters, respectively.

In addition, the center display panel 7 can be configured to display at least one of the settings, which has been specified by the operator, displayed on the pressure displays 77a, 77b, 80a and 80b, flow-rate displays 78a and 78b, and the total volume display 79.

Specifically, the controller 98 operates to send at least one of the settings, which has been specified by the operator, displayed on the pressure displays 77a, 77b, 80a, and 80b, flow-rate displays 78a and 78b, and the total volume display 79 to the system controller 5. The system controller 5 receives at least one of the settings sent from the controller 98 to display it on the center display panel 7.

The structures of the manually operable setting section 63 and the display section 64 in the front panel FP allow the operator to easily give instructions to the controller 98 and to easily visually recognize the parameters related to the abdominal cavity AC and the lumen BC.

Next, a structure of the gas supply apparatus 41 will be described hereinafter with reference to FIG. 5.

Figure 5:
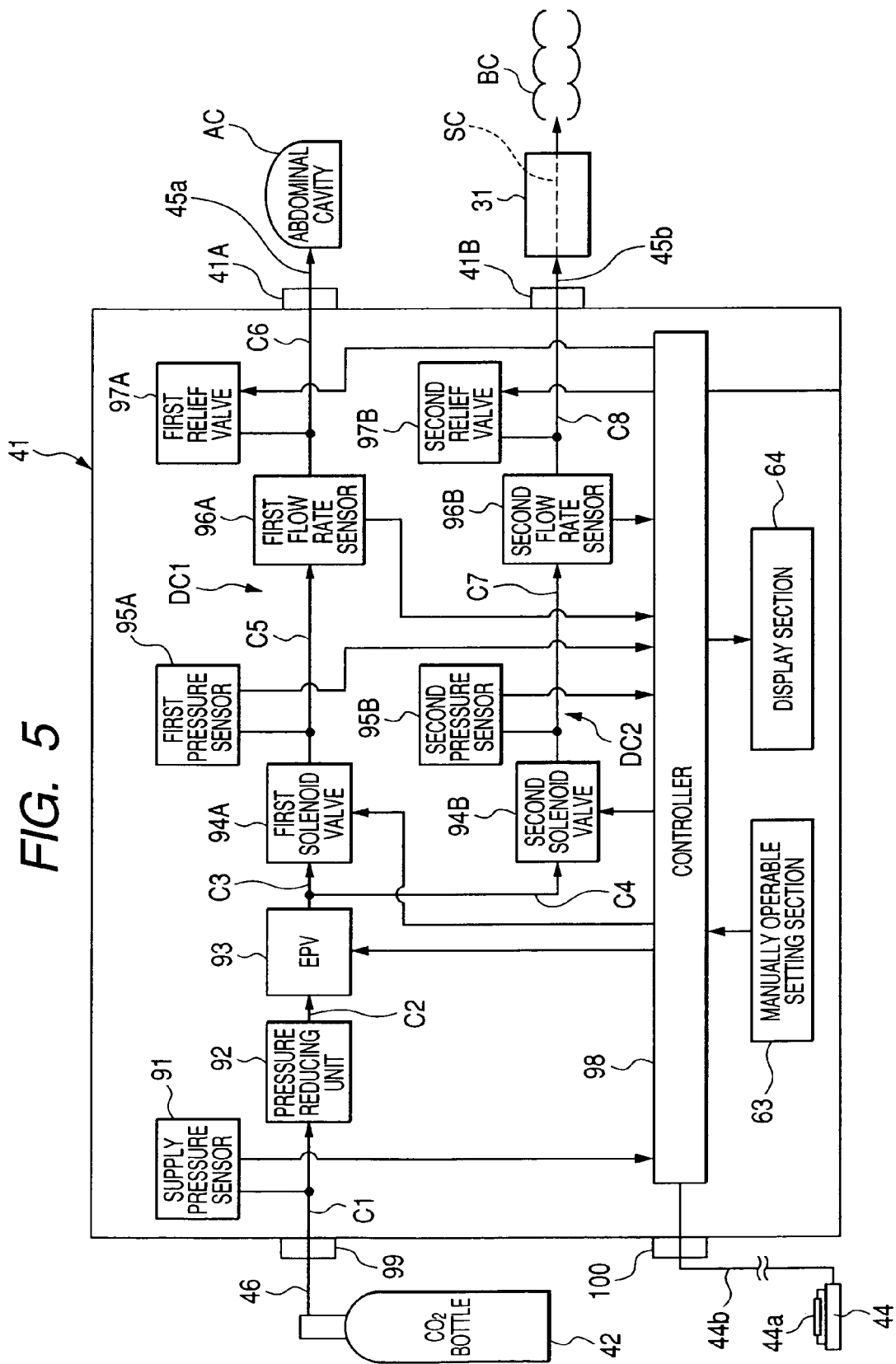
FIG. 5 is a block diagram illustrating a schematic structure of the gas supply apparatus illustrated in FIG. 1.

As shown in FIG. 5, the gas supply apparatus 41 includes a high pressure adapter 99, a first delivery channel C1, a supply pressure sensor 91, and a pressure reducing unit 92 serving as, for example, a pressure regulator. The gas supply apparatus 41 includes a second delivery channel C2, an electropneumatic proportional valve (EPV) 93 as an example of pressure regulating valves, serving as the pressure regulator, a third delivery channel C3, and a fourth delivery channel C4.

In addition, the gas supply apparatus 41 includes first and second electromagnetic valves (solenoid valves) 94A and 94B as examples of open/close valves. The first and second electromagnetic valves 94A and 94B serve as the pressure regulator.

The gas supply apparatus 41 includes a fifth delivery channel C5, a sixth delivery channel C6, the first and second pressure sensors 95A and 95B, the first flow-rate sensor 96A, and a second flow-rate sensor 96B. Moreover, the gas supply apparatus 41 includes a seventh delivery channel C7, an eighth delivery channel C8, first and second relief valves 97A and 97B, the controller 98, the manually operable setting section 63, the display section 64, and the first and second adapters 41A and 41B.

Specifically, the $CO_2$ bottle 42 has a discharge port (cock) to which one end of the high-pressure gas tube 46 is joined. The other end of the high-pressure gas tube 46 is joined to the high-pressure adapter 99. The high-pressure adapter 99 is joined to an inlet of the pressure reducing unit 92 via the first delivery channel C1. The supply pressure sensor 91 is attached to the first delivery channel C1. An outlet of the pressure reducing unit 92 is coupled to an inlet of the electropneumatic proportional valve 93 via the second delivery channel C2. An outlet of the electropneumatic proportional valve 93 is branched into the third delivery channel C3 for the abdominal cavity AC and the fourth delivery channel C4 for the lumen BC.

One branched channel C3 is coupled to an inlet of the first solenoid valve 94A. An outlet of the first solenoid valve 94A is coupled to the fifth delivery channel C5 to which the first pressure sensor 95A is attached. The fifth delivery channel C5 is coupled to an inlet of the first flow rate sensor 96A whose outlet is coupled through the sixth delivery channel C6 and the first adapter 41A to the one end of the abdominal cavity tube 45$a$. The other end of the tube 45$a$ is coupled to the third trocar 16, and the third trocar 16 is inserted into the abdominal cavity AC of the patient 10.

The other branched channel C4 is coupled to an inlet of the second solenoid valve 94B via the seventh delivery channel C7. An outlet of the second solenoid valve 94B is coupled to the eighth delivery channel C8. The eighth delivery channel C8 is coupled to an inlet of the second flow rate sensor 96B whose outlet is coupled through the eighth delivery channel C8 to the second adapter 41B. The second adapter 41B is coupled to the one end of the lumen tube 45$b$. The other end of the tube 45$b$ is communicably coupled to the gas delivery channel SC formed inside the flexiblescope 31 through the tube coupler 43$a$, and the insertion portion 34 of the flexiblescope 31 is inserted into the lumen BC of the patient 10.

In the embodiment, the third delivery channel C3, the first solenoid valve 94A, the fifth delivery channel C5, the first flow-rate sensor 95A, the sixth delivery channel C6, the first adapter 41A, and the abdominal cavity tube 45$a$ constitute a first $CO_2$ supply path DC1 directing the carbon dioxide gas into the abdominal cavity AC. Specifically, the first solenoid valve 94A is provided in the first $CO_2$ supply path DC1.

Similarly, the fourth delivery channel C4, the second solenoid valve 94B, the seventh delivery channel C7, the second flow-rate sensor 96B, the eighth delivery channel C8, the second adapter 41B, and the lumen tube 45$b$ constitute part of a second $CO_2$ supply path DC2. The second $CO_2$ supply path DC2 is configured to direct the carbon dioxide gas into the lumen BC. Specifically, the second solenoid valve 94B is provided in the second $CO_2$ supply path DC2.

The gas supply apparatus 41 has the foot switch cable 44$b$ electrically connected to a switch connector 100; the foot switch cable 44$b$ is electrically connected to the foot switch 44. The switch connector 100 is electrically connected to the controller 98. With the electrical connection between the foot switch 44 and the controller 98, the depressing operation of the switch portion 44$a$ by the operator allows the instruction to be provided through the foot switch cable 44$b$ to the controller 98. Incidentally, communications between the foot switch 44 and the controller 98 can be wirelessly established.

Specifically, when the cock of the $CO_2$ bottle 42 is opened, carbon dioxide stored therein in a liquid form is vaporized to form the carbon dioxide gas. The carbon dioxide gas is delivered to the pressure reducing unit 92 through the high-pressure gas tube 46, the high pressure adapter 99, and the first delivery channel C1 of the gas supply apparatus 41. The carbon dioxide gas is reduced in pressure by the pressure reducing unit 92 to have a predetermined pressure, and thereafter, guided via the second delivery channel C2 to the electropneumatic proportional valve 93. The electropneumatic proportional valve 93 regulates the pressure of the carbon dioxide gas to a pressure within a range suitable for supply into the inside of the abdominal cavity AC or that of the lumen BC.

More particularly, the electropneumatic proportional valve 93 is provided with a solenoid composed of, for example, a magnet coil (solenoid coil) and a compass needle, which are not shown. The electropneumatic proportional valve 93 is provided with a thin film for pressure control, and a pressure reducing spring. The solenoid is electrically connected to the controller 98. The electropneumatic proportional valve 93 is configured such that the solenoid controls force applied on the thin film by the pressure reducing spring depending on a control signal applied from the controller 40, thereby regulating the pressure of the carbon dioxide gas.

Specifically, the electropneumatic proportional valve 93 is designed to change its opening in proportional to a voltage or a current as the control signal applied from the controller 98 so as to regulate the pressure and the flow-rate of the carbon dioxide gas flowing therethrough within the corresponding appropriate ranges, respectively For example, the electropneumatic proportional valve 93 allows the pressure of the carbon dioxide gas to be regulated within a range from 0 to 500 mmHg based on the control signal applied from the controller 98.

For example, the range of the pressure of the carbon dioxide gas to be insufflated into the abdominal cavity AC is preferably 0 to 80 mmHg or thereabout; the range of the flow-rate thereof to be insufflated thereinto is preferably 0.1 to 35 L/min or thereabout. Moreover, for example, the range of the pressure of the carbon dioxide gas to be insufflated into the lumen BC is preferably 100 to 500 mmHg or thereabout; the range of the flow-rate thereof to be insufflated thereinto is preferably 1 to 3 L/min or thereabout.

The carbon dioxide gas whose pressure is regulated by the electropneumatic proportional valve 93 is divided into two parts, and they are introduced into the third and fourth delivery channels C3 and C4, respectively. The third and fourth delivery channels C3 and C4 constitute bifurcating channels, respectively. The divided parts of the carbon dioxide gas are introduced into two supply paths constituting the first $CO_2$ supply path DC1 directing the carbon dioxide gas into the abdominal cavity AC and the second $CO_2$ supply path DC2 directing it into the lumen BC, respectively.

Specifically, the downstream side of the electropneumatic proportional valve 93 is separated into the first $CO_2$ supply path DC1 and the second $CO_2$ supply path DC2 through the third and fourth delivery channels C3 and C4.

Incidentally, in the first embodiment, a first delivery member of the present invention corresponds to at least the fifth and sixth delivery channels C5 and C6 in the first $CO_2$ supply path DC1. Specifically, the concept of the first delivery member of the present invention can expand to cover the whole of the first $CO_2$ supply path DC1 depending on aspects of the gas supply apparatus 41.

Likewise, in the first embodiment, a second delivery member of the present invention corresponds to at least the seventh and eighth delivery channels C7 and C8 in the second $CO_2$ supply path DC2. Specifically, the concept of the second delivery member of the present invention can expand to cover the whole of the second $CO_2$ supply path DC2 depending on aspects of the gas supply apparatus 41.

The supply pressure sensor 91 is electrically connected to the controller 98. The supply pressure sensor 91 has a function of detecting the pressure of the carbon dioxide gas flowing from the $CO_2$ bottle 42 to the first delivery channel C1 to send the detected result (detected pressure value) to the controller 98.

The first pressure sensor 95A is electrically connected to the controller 98. The first pressure sensor 95A has a function of measuring a pressure in the fifth delivery channel C5, in other words, a pressure inside the abdominal cavity AC, thereby sending the measured result to the controller 98.

The second pressure sensor 95B is electrically connected to the controller 98. The second pressure sensor 95B has a function of measuring a pressure in the seventh delivery channel C7, in other words, a pressure inside the lumen BC thereby sending the measured result to the controller 98.

Each of the first and second solenoid valves 94A and 94B is electrically connected to the controller 98 and configured to open and close based on control signals sent from the controller 98. The opening and closing of the first solenoid valve 94A allow first $CO_2$ supply path DC1 to open and close, respectively. Similarly, the opening and closing of the second solenoid valve 94B permit the second $CO_2$ supply path DC2 to open and close, respectively.

The first and second flow rate sensors 96A and 96B are electrically connected to the controller 98. The first flow rate sensor 96A has a function of detecting the flow rate of the carbon dioxide gas flowing through the first solenoid valve 94A and the fifth delivery channel C5. Similarly, the second flow rate sensor 94B is operative to detect the flow rate of the carbon dioxide gas flowing through the second solenoid valve 94B and the seventh delivery channel C7. Each of the first and second flow rate sensors 96A and 96B is configured to send the detected result to the controller 98.

Furthermore, the first relief valve 97A is disposed at the midstream of the sixth delivery channel C6 between the first flow rate sensor 96A and the first adapter 41A. The first relief valve 97A is electrically connected to the controller 98. The first relief valve 97A is operative to remain in a closed state, and to open based on a control signal sent from the controller 98. The opening of the first relief valve 97A causes carbon dioxide gas in the abdominal cavity AC to be released, thereby reducing a pressure inside the abdominal cavity AC.

Similarly, the second relief valve 97B is disposed at the midstream of the eighth delivery channel C8 between the second flow rate sensor 96B and the second adapter 41B. The second relief valve 97B is electrically connected to the controller 98. The second relief valve 97B is operative to remain in a closed state, and to open based on a control signal sent from the controller 98. The opening of the second relief valve 97B causes carbon dioxide gas in the lumen BC to be released, thereby reducing a pressure inside the lumen BC.

The controller 98 is operative to receive the measured values outputted from the supply pressure sensor 91, the first and second pressure sensors 95A and 95B, the first and second flow rate sensors 96A and 96B. The controller 98 is programmed to execute opening control (pressure control) of the electropneumatic proportional valve 93, opening and closing controls of each of the first and second solenoid valves 94A and 94B, and display control of the display section 64 based on the received measured values.

In addition, the manually operable setting section 63 is electrically connected to the controller 98. The controller 98 is also programmed to execute opening control (pressure control) of the electropneumatic proportional valve 93, opening and closing controls of each of the first and second solenoid valves 94A and 94B, and display control of the display section 64 based on the instructions sent from the manually operable setting section 63.

Specifically, when the cock of the $CO_2$ bottle 42 is opened, carbon dioxide stored therein in a liquid form is vaporized to form the carbon dioxide gas. The carbon dioxide gas is delivered to the pressure reducing unit 92 through the high-pressure gas tube 46, the high pressure adapter 99, and the first delivery channel C1 of the gas supply apparatus 41. The carbon dioxide gas is reduced in pressure by the pressure reducing unit 92 to have the predetermined pressure. Thereafter, the carbon dioxide gas is delivered to the electropneumatic proportional valve 93 so that the pressure and flow-rate is regulated based on the control signals sent from the controller 98.

The carbon dioxide gas with its pressure and flow-rate regulated is selectively switched to either the first $CO_2$ supply path DC1 or the second $CO_2$ supply path DC2. The carbon dioxide gas, which is switched to the first $CO_2$ supply path DC1, is supplied into the abdominal cavity AC therethrough; the carbon dioxide gas, which is switched to the second $CO_2$ supply path DC2, is supplied into the lumen BC therethrough.

Incidentally, in the first embodiment, the channels and the like constituting the first $CO_2$ supply path DC1 provide airtight junction therebetween, and the channels and the like constituting the second $CO_2$ supply path DC2 provide airtight junction therebetween.

In the first embodiment, as shown in FIG. 1, the adapter 43 corresponds to the communicable connecting location of the lumen tube 45b with respect to the gas delivery channel SC inside the manipulator 35. This configuration allows the adapter 43 to be arranged at a position closer to the insertion section 34 than the gas and water supply switch 35a through which the through hole is formed.

Specifically, in the first embodiment, the through hole of the gas and water supply switch 35a of the manipulator 35 of the flexiblescope 31 deviates from the second $CO_2$ supply path DC2 including the lumen tube 45b through which the carbon dioxide gas is supplied. Thus, in the first embodiment, the operator is able to perform the operations to supply the carbon dioxide gas into the lumen BC and to interrupt the supply thereof by the operations to depress the switch portion 44a of the foot switch 44 and release it without opening and closing the through hole in the switch 35a.

Next, operations of the gas supply apparatus 41 according to the first embodiment will be described hereinafter.

When using the gas supply apparatus 41, an assistant, such as a nurse, prepares the abdominal cavity tube 45a to couple the one end of the tube 45a to the first adapter 41A of the gas supply apparatus 41 and the other end thereof to the third trocar 16, respectively. Next, the assistant attaches the adapter 43 to the base 38 of the flexiblescope 31, and prepares the lumen tube 45b to couple the one end of the tube 45b to the second adapter 41B of the gas supply apparatus 41 and the other end thereof to the tube coupling portion 43a of the adapter 43, respectively.

Subsequently, before surgery, the assistant opens the cock of the $CO_2$ bottle 42. The opening of the cock of the $CO_2$ bottle 42 causes the carbon dioxide gas to flow out of the bottle 42 through the high-pressure gas tube 46 so as to flow into the gas supply apparatus 41. The gas flowing into the apparatus 41 is introduced through the first delivery channel C1 to the pressure reducing unit 92.

The carbon dioxide gas is reduced in pressure by the pressure reducing unit 92 to have the predetermined pressure, thereby being guided via the second delivery channel C2 to the inlet of the electropneumatic proportional valve 93.

Under a state before surgery, the electropneumatic proportional valve 93 remains closed, which causes the carbon dioxide gas not to flow the downstream thereof.

Next, the power switch 71 is turned on by, for example, the operator. In response to the turning-on of the switch 71, the pressure display 77a of the front panel FP is ready to display the measured value by the first pressure sensor 95A, and the pressure display 80a of the front panel FP is ready to display the measured value by the second pressure sensor 95B. In addition, the foot switch 44 becomes a state that allows the operator to operate it.

On the pressure display 77b, the pressure setting inside the abdominal cavity AC, which is previously set on, for example, the center operation panel 8, is displayed. Similarly, on the flow-rate display 78b, the flow-rate setting of the carbon dioxide gas to be insufflated into the abdominal cavity AC, which is previously set on, for example, the center operation panel 8, is displayed.

Furthermore, on the pressure display 80b, the pressure setting of the carbon dioxide gas to be insufflated into the lumen BC, which is previously set on, for example, the center operation panel 8, is displayed.

The supply pressure sensor 91 measures the pressure supplied from the $CO_2$ bottle 42 to the pressure reducing unit 92 through the first delivery channel C1 to send the measured value to the controller 98. As a result, the controller 98 calculates the volume of the carbon dioxide gas remaining in the $CO_2$ bottle 42 to display it on the gas remaining volume indicators 76.

In cases where no pressure setting inside the abdominal cavity AC is previously determined on the center operating panel 8, the operator appropriately operates the pressure setting buttons 74a and 74b to determine the pressure setting inside the abdominal cavity AC. The instruction corresponding to the pressure setting inside the abdominal cavity AC is sent from the manually operable setting section 63 to the controller 98. Similarly, in cases where no flow-rate settings for the insufflations into the abdominal cavity AC are previously determined on the center operating panel 8, the operator appropriately operates the flow-rate setting buttons 75a and 75b. The instruction corresponding to the flow-rate setting for insufflation into the abdominal cavity AC is sent from the manually operable setting section 63 to the controller 98.

In addition, no pressure setting inside the lumen BC is previously determined on the center operating panel 8, the operator appropriately operates the pressure setting buttons 81a and 81b to determine the pressure setting inside the lumen BC. The instruction corresponding to the pressure setting inside the lumen BC is sent from the manually operable setting section 63 to the controller 98.

Subsequently, under laparoscopic surgery, the operator inserts the rigidscope 21 into the inside of the abdominal cavity AC with the flexiblescope 31 being inserted into the lumen BC, such as a large intestine present in the abdominal cavity AC. The operator specifies and treats at least one site to be treated in the abdominal cavity AC and/or the lumen BC based on the first and second images picked up by the rigidscope 21 and the flexiblescope 31, respectively.

Operations of the abdominal cavity select button 82 and the gas-supply start button 72 allow the controller 98 to start insufflation of the carbon dioxide gas with its pressure regulated suitable for the abdominal cavity AC thereinto. Specifically, the controller 98 continuously controls the pressure and the flow-rate inside the abdominal cavity AC so that they are approximately close to the pressure setting and flow-rate setting established on the font panel FP, respectively.

On the other hand, operations of the lumen select button 83 and the foot switch 44 allow the controller 98 to start insufflation of the carbon dioxide gas with its pressure regulated suitable for the lumen BC thereinto. Specifically, the controller 98 continuously controls the pressure inside the lumen BC so that it is approximately close to the pressure setting established on the font panel FP.

Next, an example of control operations of the controller 98 of the gas supply apparatus 41 when insufflating the carbon dioxide gas into each of the abdominal cavity AC and the lumen BC will be described hereinafter with reference to FIG. 6.

Figure 6:
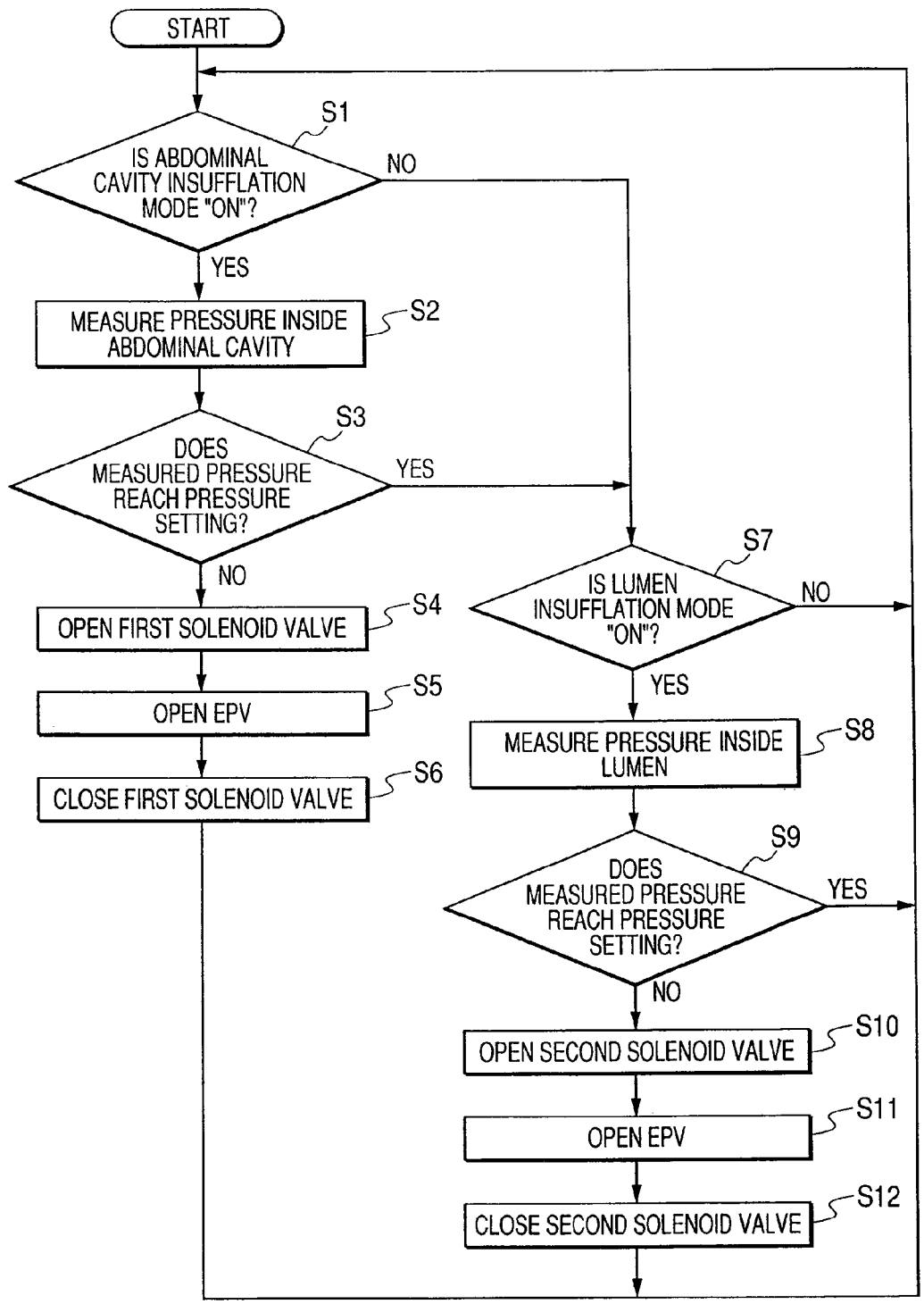
FIG. 6 is a flowchart schematically illustrating an example of control operations of a controller illustrated in FIG. 5.

At first, the controller 98 determines whether the abdominal cavity select button 82 is turned on, in other words, its operation mode is the abdominal-cavity insufflation mode (FIG. 6; step S1).

When the abdominal cavity select button 82 is in on state, the controller 98 determines its operation mode is the abdominal-cavity insufflation mode, in other words, the determination in step S1 is YES so that the controller 98 enters the abdominal-cavity insufflation mode.

In the abdominal-cavity insufflation mode, while the gas-supply start button 73 is in on state, the controller 98 sends the control signals to the electropneumatic proportional valve 93 and the first solenoid valve 93A, respectively. The control signal sent to the electropneumatic proportional valve 93 allows it to open by a predetermined opening and the control signal sent to the first solenoid valve 94A allows it to open. As a result, the carbon dioxide gas supplied up to the inlet of the electropneumatic proportional valve 93 to flow through the electropneumatic proportional valve 93 so that the pressure and the flow-rate of the carbon dioxide gas are regulated within the corresponding predetermined ranges suitable for the insufflation of the abdominal cavity AC, respectively. The carbon dioxide gas with its pressure and flow-rate being regulated, respectively, passes through the first solenoid valve 94A to be supplied into the abdominal cavity AC through the first adapter 41A, the abdominal cavity tube 45a, and the third trocar 16.

Incidentally, because the second solenoid valve 94B is closed, no carbon dioxide gas is supplied to the second $CO_2$ supply path DC2 for the lumen BC.

Specifically, the controller 98 obtains the pressure value inside the abdominal cavity AC based on the pressure measured by the first pressure sensor 95A with the first solenoid valve 94A closed, thereby displaying the obtained pressure value on the pressure display 77a in step S2.

The controller 98 determines whether the obtained pressure value reaches the pressure setting set on the front panel FP and displayed on the pressure display 77b or thereabout (step S3).

When determining that the obtained pressure does not reach the pressure setting, that is, the determination in step S3 is NO, the controller 98 calculates the difference between the obtained pressure and the pressure setting to determine a pressure reduction value of the electropneumatic proportional valve 93 based on the calculated difference.

Subsequently, the controller 98 sends the control signal to the first solenoid valve 94A to open it (step S4). Next, the controller 98 sends the control signal to the electropneumatic proportional valve 93 to open it by a predetermined opening corresponding to the determined pressure reduction value (step S5).

As a result, the carbon dioxide gas, which is reduced in pressure to the predetermined pressure by the pressure reduction unit 92, is supplied into the abdominal cavity AC through the first $CO_2$ supply path DC 1. Specifically, the carbon dioxide gas with the predetermined pressure is supplied through the electropneumatic proportional valve 93, the third flow channel C3, the first solenoid valve 94A, the fifth flow channel C5, the first flow rate sensor 96A, the sixth flow channel C6, and the first adapter 41A. Thereafter, the carbon dioxide gas with the predetermined pressure is delivered through the abdominal cavity tube 45a and the third trocar 16 to be supplied into the abdominal cavity AC.

Under such a gas supply state, the measured result of the first pressure sensor 95A and that of the first flow-rate sensor 96A are sent to the controller 98. The controller 98 adjusts the opening of the electropneumatic proportional valve 93 so as to regulate the pressure of the carbon dioxide gas flowing therethrough within the corresponding appropriate range of, for example, 0 to 80 mmHg or thereabout. Simultaneously, the controller 98 adjusts the opening of the electropneumatic proportional valve 93 so as to regulate the flow-rate of it within the corresponding appropriate range of, for example, 0.1 to 35 L/min or thereabout in step S5.

After a predetermined period of time has elapsed, the controller 98 sends the control signal to the first solenoid valve 94A to close it, thereby interrupting the insufflation of the carbon dioxide gas into the abdominal cavity AC (step S6), returning to step S1. Thus, the controller 98 repeatedly executes the carbon dioxide gas supply and interruption control operations for the abdominal cavity AC shown in steps S1 to S6 until the pressure measured by the first pressure sensor 95A in step S2 reaches the pressure setting set on the front panel FP or thereabout.

The whole of the carbon dioxide gas supply and interruption control operations for the abdominal cavity AC is referred to as "abdominal-cavity pressure control operations".

On the other hand, while the abdominal cavity select button 82 is in off state, in other words, the operation mode of the controller 98 is not in the abdominal-cavity insufflation mode (the determination in step S1 is NO), the controller 98 shifts to step S7. Similarly, when the abdominal cavity pressure reaches the pressure setting or thereabout, so that the determination in step S3 is YES, the controller 98 shift to step S7.

In step S7, the controller 98 determines whether the lumen select button 83 is turned on, in other words, its operation mode is the lumen insufflation mode.

When the lumen select button 83 is in on state, the controller 98 determines its operation mode is the lumen insufflation mode, in other words, the determination in step S7 is YES so that the controller 98 enters the lumen insufflation mode.

In the lumen insufflation mode, while the switch portion 44a of the foot switch 44 is in on state, the controller 98 sends the control signals to the electropneumatic proportional valve 93 and the second solenoid valve 93B, respectively. The control signal sent to the electropneumatic proportional valve 93 allows it to open by a predetermined opening and the control signal sent to the second solenoid valve 94B allows it to open. As a result, the carbon dioxide gas supplied up to the inlet of the electropneumatic proportional valve 93 to flow through the electropneumatic proportional valve 93 so that the pressure and the flow-rate of the carbon dioxide gas are regulated within the corresponding predetermined ranges suitable for the insufflation of the lumen BC, respectively. The carbon dioxide gas with its pressure and flow-rate being regulated, respectively, passes through the second solenoid valve 94B to be supplied into the lumen BC through the second adapter 41B, the lumen tube 45b, the adapter 43, and the gas delivery channel SC inside the flexiblescope 31.

Incidentally, because the first solenoid valve 94A is closed, no carbon dioxide gas is supplied to the first $CO_2$ supply path DC1 for the abdominal cavity AC.

Specifically, the controller 98 obtains the pressure value inside the lumen BC based on the pressure measured by the second pressure sensor 95B with the second solenoid valve 94B closed, thereby displaying the obtained pressure value on the pressure display 80a in step S8.

The controller 98 determines whether the obtained pressure value reaches the pressure setting set on the front panel FP and displayed on the pressure display 80b or thereabout (step S9).

When determining that the obtained pressure does not reach the pressure setting, that is, the determination in step S9 is NO, the controller 98 calculates the difference between the obtained pressure and the pressure setting to determine a pressure reduction value of the electropneumatic proportional valve 93 based on the calculated difference.

Subsequently, the controller 98 sends the control signal to the second solenoid valve 94B to open it (step S10). Next, the controller 98 sends the control signal to the electropneumatic proportional valve 93 to open it by a predetermined opening corresponding to the determined pressure reduction value (step S11).

As a result, the carbon dioxide gas, which is reduced in pressure to the predetermined pressure by the pressure reduction unit 92, is supplied into the lumen BC through the second $CO_2$ supply path DC2. Specifically, the carbon dioxide gas with the predetermined pressure is supplied through the electropneumatic proportional valve 93, the fourth flow channel C4, the second solenoid valve 94B, the seventh flow channel C7, the second flow rate sensor 96B, the eighth flow channel C8, and the second adapter 41B. Thereafter, the carbon dioxide gas with the predetermined pressure is delivered through the lumen tube 45b, the flexible scope 31 and the like to be supplied into the lumen BC.

Under such a gas supply state, the measured result of the second pressure sensor 95B and that of the second flow-rate sensor 96B are sent to the controller 98. The controller 98 adjusts the opening of the electropneumatic proportional valve 93 so as to regulate the pressure of the carbon dioxide gas flowing therethrough within the corresponding appropriate range of, for example, 0 to 500 mmHg or thereabout. Simultaneously, the controller 98 adjusts the opening of the electropneumatic proportional valve 93 so as to regulate the flow-rate of it within the corresponding appropriate range of, for example, 1 to 3 L/min or thereabout in step S11.

After a predetermined period of time has elapsed, the controller 98 sends the control signal to the second solenoid valve 94B to close it, thereby interrupting the insufflation of the carbon dioxide gas into the lumen BC (step S12), returning to step S1. Thus, the controller 98 repeatedly executes the carbon dioxide gas supply and interruption control operations for the lumen BC shown in steps S1, S7 to S12 until the pressure measured by the second pressure sensor 95B in step S8 reaches the pressure setting set on the front panel FP or thereabout.

The whole of the carbon dioxide gas supply and interruption control operations for the lumen BC is referred to as "luminal pressure control operations".

The controller 98 executes both the abdominal-cavity pressure control operations shown in steps S1 to S6 and the luminal pressure control operations shown in steps S7 to S12. This allows the carbon dioxide gas to be insufflated into the abdominal cavity AC with its pressure regulated suitable therefore, and to be insufflated into the lumen BC with its pressure regulated suitable therefore.

Specifically, the controller 98 executes the abdominal-cavity pressure control operations shown in steps S1 to S6 when the pressure inside the abdominal cavity AC falls down from the pressure setting therefore and executes the luminal pressure control operations shown in steps S7 to S12 when the pressure inside the lumen BC falls down from the pressure setting therefore.

Figure 7:
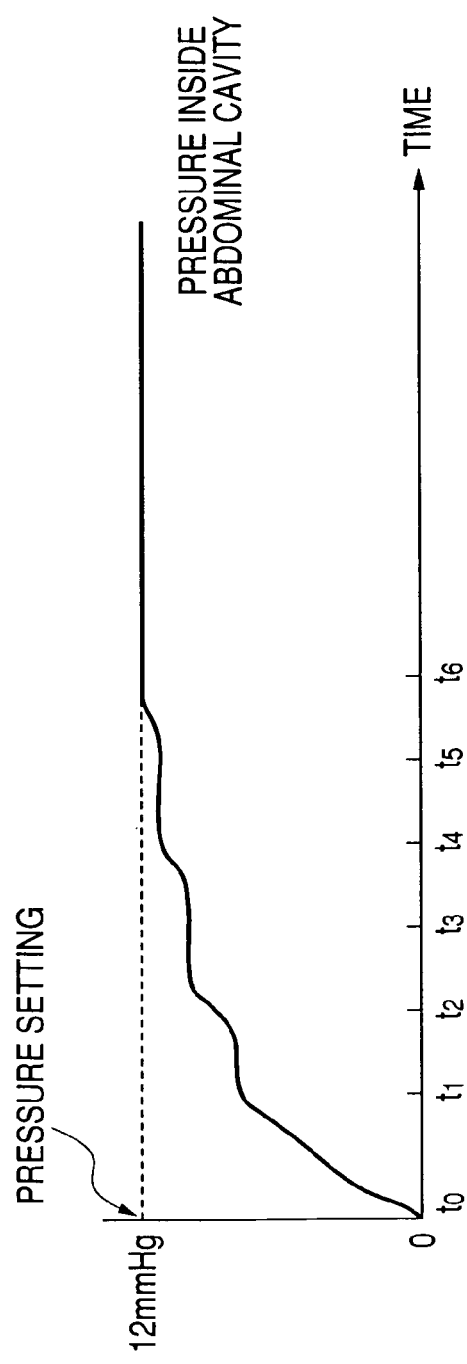
FIG. 7 is a graph schematically illustrating the change of pressure inside an abdominal cavity in time according to the first embodiment.
Figure 8:
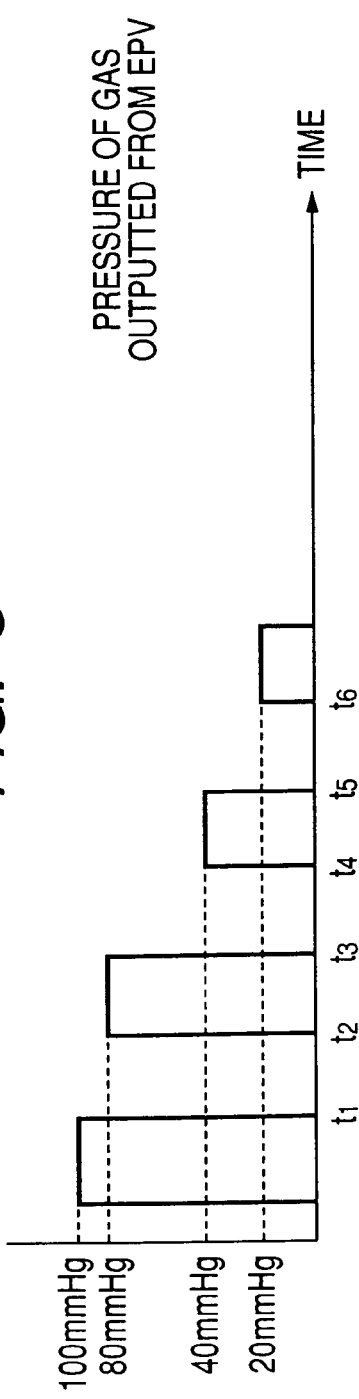
FIG. 8 is a graph schematically illustrating the change of pressure of gas outputted from an electropneumatic proportional valve and directing toward the abdominal cavity in time according to the first embodiment.

For example, in the first embodiment, the pressure inside the abdominal cavity AC is controlled as shown in FIG. 7. In the example, the pressure setting for the abdominal cavity AC set on the front panel FP is 12 mmHg. The pressure of the carbon dioxide gas outputted from the electropneumatic proportional valve 93 is regulated, for example, as shown in FIG. 8. That is, the pressure inside the abdominal cavity AC rises in time (t0, t1, . . . , t6) so that it approximately reaches the pressure setting of 12 mmHg at time t6. In addition, FIGS. 7 and 8 show that the pressure inside the abdominal cavity AC rises in time with decreasing pressure of the carbon dioxide gas outputted from the electropneumatic proportional valve 93 in time.

Figure 9:
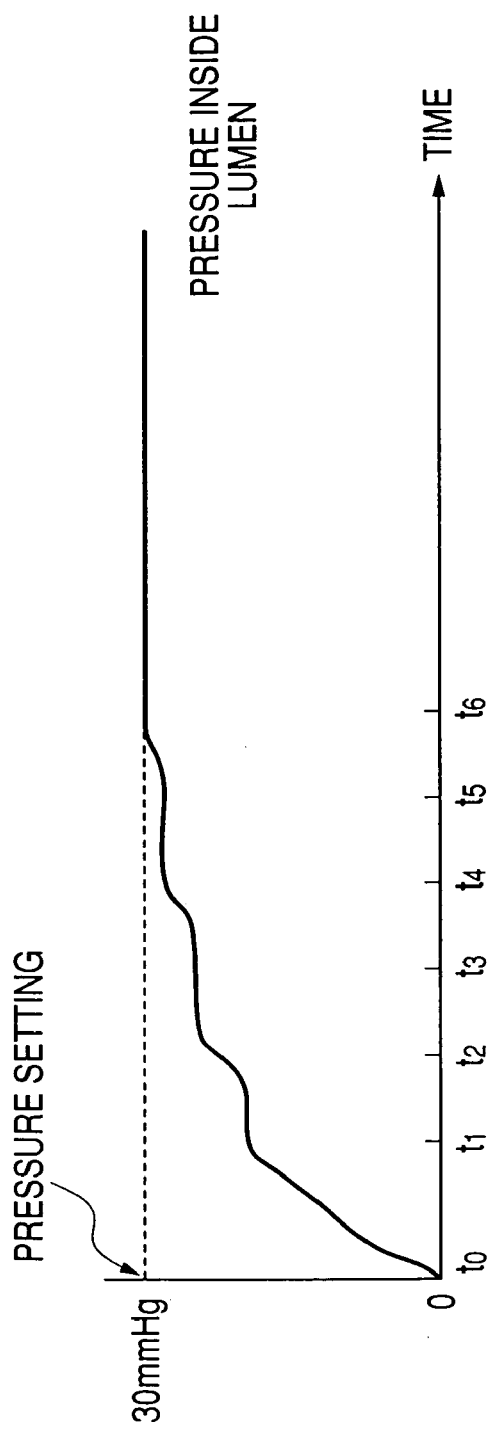
FIG. 9 is a graph schematically illustrating the change of pressure inside a lumen in time according to the first embodiment.
Figure 10:
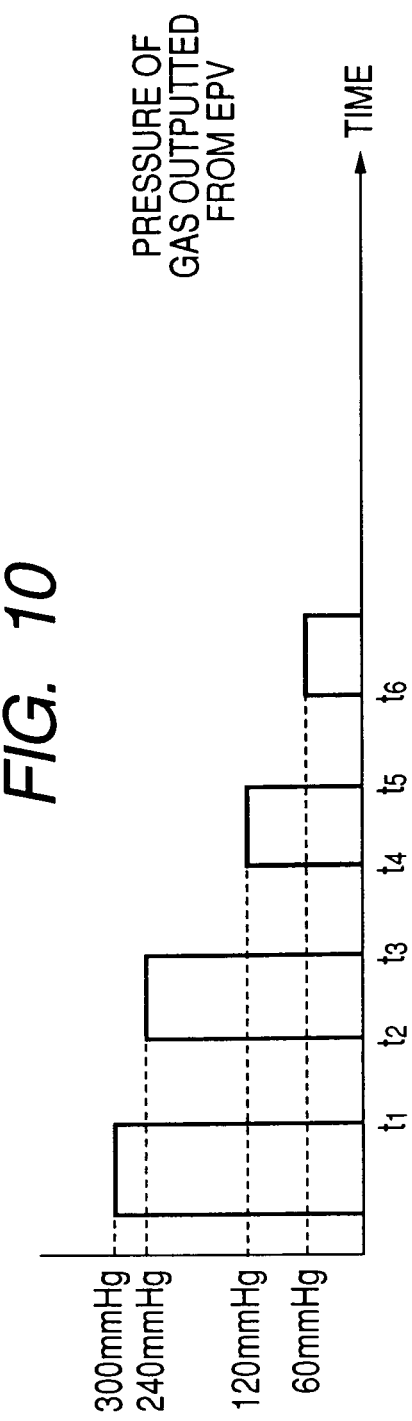
FIG. 10 is a graph schematically illustrating the change of pressure of gas outputted from the electropneumatic proportional valve and directing toward the lumen in time according to the first embodiment.

Similarly, for example, the pressure inside the lumen BC is controlled as shown in FIG. 9. In the example, the pressure setting for the lumen BC set on the front panel FP is 30 mmHg. The pressure of the carbon dioxide gas outputted from the electropneumatic proportional valve 93 is regulated, for example, as shown in FIG. 10. That is, the pressure inside the lumen BC rises in time (t0, t1, . . . , t6) so that it approximately reaches the pressure setting of 30 mmHg at time t6. In addition, FIGS. 9 and 10 show that the pressure inside the lumen BC rises in time with decreasing pressure of the carbon dioxide gas outputted from the electropneumatic proportional valve 93 in time.

As set forth above, the first embodiment allows single gas supply apparatus 41 to serve as both an insufflator and an endoscope $CO_2$ regulator (ECR). Specifically, the gas supply apparatus 41 executes both the abdominal-cavity pressure control operations to insufflate the carbon dioxide gas into the abdominal cavity AC with its pressure regulated suitable therefore and the luminal pressure control operations to insufflate the carbon dioxide gas into the lumen BC with its pressure regulated suitable therefore.

The first embodiment of the invention therefore makes it possible to reduce the size and the cost of the gas supply apparatus 41, as compared with a gas supply apparatus having individually prepared insufflator and an ECR.

Second Embodiment

The configuration of a surgical system with a gas supply apparatus according to a second embodiment of the present invention is substantially identical to that of the surgical system 1 according to the first embodiment. Reference numerals assigned to elements of the surgical system according to the second embodiment, which are substantially identical to those of the surgical system 1, are the same as those assigned to the elements of the surgical system 1.

The second embodiment has characterized control operations of the controller 98 when the measured pressure inside the abdominal cavity AC or that inside the lumen falls down from a corresponding pressure setting.

Figure 11:
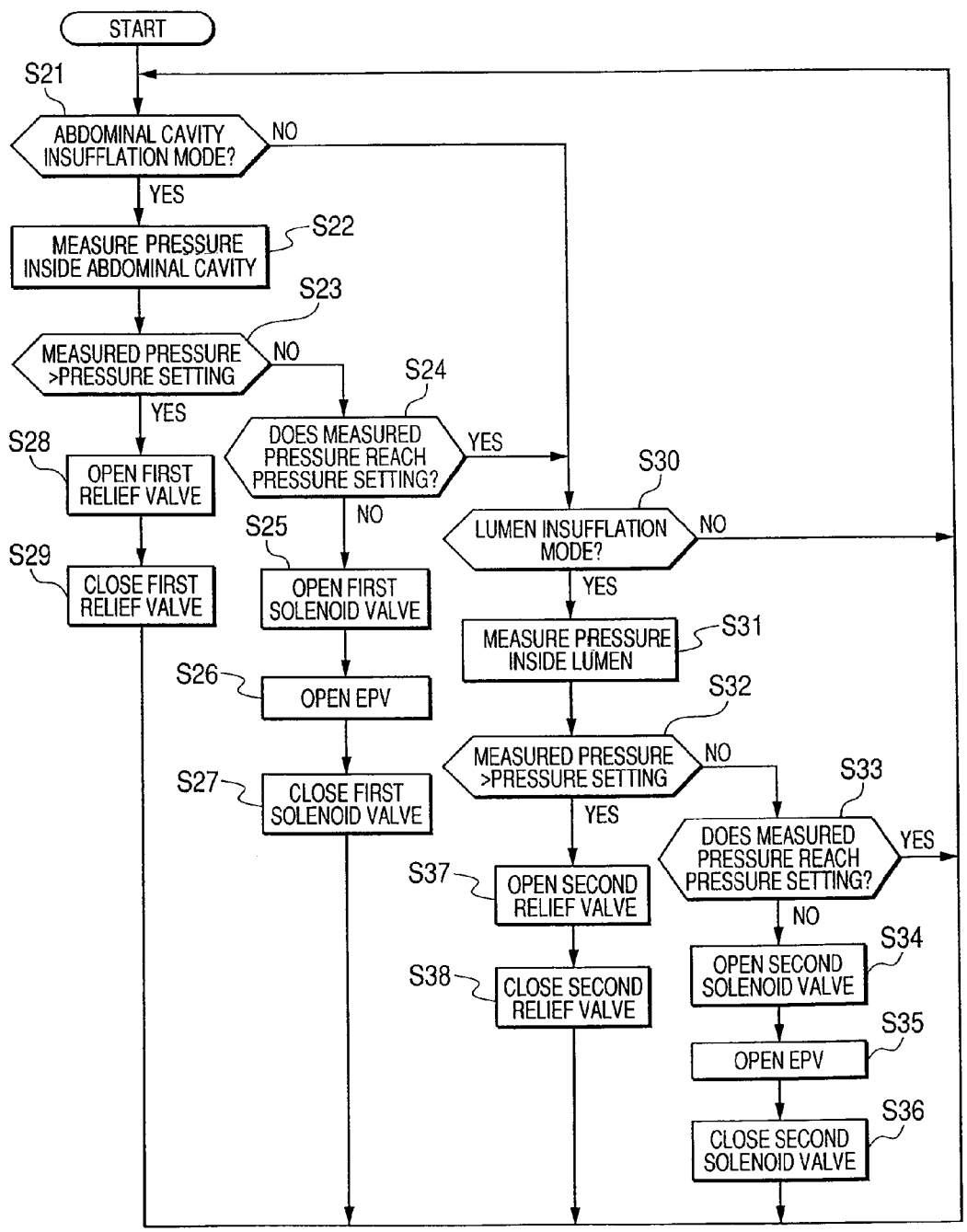
FIG. 11 is a flowchart schematically illustrating an example of control operations of a controller according to a second embodiment of the invention.

As shown in FIG. 11, the controller 98 determines whether the abdominal cavity select button 82 is turned on, in other words, its operation mode is the abdominal-cavity insufflation mode (FIG. 11; step S21).

When the abdominal cavity select button 82 is in on state, the controller 98 determines its operation mode is the abdominal-cavity insufflation mode, in other words, the determination in step S21 is YES so that the controller 98 enters the abdominal-cavity insufflation mode.

In the abdominal-cavity insufflation mode, while the gas-supply start button 73 is in on state, the controller 98 sends the control signals to the electropneumatic proportional valve 93 and the first solenoid valve 93A, respectively. The control signal sent to the electropneumatic proportional valve 93 allows it to open by a predetermined opening and the control signal sent to the first solenoid valve 94A allows it to open. As a result, the carbon dioxide gas supplied up to the inlet of the electropneumatic proportional valve 93 to flow through the electropneumatic proportional valve 93 so that the pressure and the flow-rate of the carbon dioxide gas are regulated within the corresponding predetermined ranges suitable for the insufflation of the abdominal cavity AC, respectively. The carbon dioxide gas with its pressure and flow-rate being regulated, respectively, passes through the first solenoid valve 94A to be supplied into the abdominal cavity AC through the first adapter 41A, the abdominal cavity tube 45a, and the third trocar 16.

Incidentally, because the second solenoid valve 94B is closed, no carbon dioxide gas is supplied to the second $CO_2$ supply path DC2 for the lumen BC.

Specifically, the controller 98 obtains the pressure value inside the abdominal cavity AC based on the pressure measured by the first pressure sensor 95A with the first solenoid valve 94A closed, thereby displaying the obtained pressure value on the pressure display 77a in step S22.

The controller 98 determines whether the obtained pressure value is higher than the pressure setting set on the front panel FP and displayed on the pressure display 77b (step S23).

When determining that the obtained pressure is lower than the pressure setting, that is, the determination in step S23 is NO, the controller 98 determines whether the obtained pressure value reaches the pressure setting set on the front panel FP and displayed on the pressure display 77b or thereabout (step S24).

When determining that the obtained pressure does not reach the pressure setting, that is, the determination in step S24 is NO, the controller 98, as well as the first embodiment, calculates the difference between the obtained pressure and the pressure setting to determine a pressure reduction value of the electropneumatic proportional valve 93 based on the calculated difference.

Subsequently, the controller 98 sends the control signal to the first solenoid valve 94A to open it (step S25). Next, the controller 98 sends the control signal to the electropneumatic proportional valve 93 to open it by a predetermined opening corresponding to the determined pressure reduction value.

As a result, the carbon dioxide gas, which is reduced in pressure to the predetermined pressure by the pressure reduction unit 92, is supplied into the abdominal cavity AC through the first $CO_2$ supply path DC 1. Specifically, the carbon dioxide gas with the predetermined pressure is supplied through the electropneumatic proportional valve 93, the third flow channel C3, the first solenoid valve 94A, the fifth flow channel C5, the first flow rate sensor 96A, the sixth flow channel C6, and the first adapter 41A. Thereafter, the carbon dioxide gas with the predetermined pressure is delivered through the abdominal cavity tube 45a and the third trocar 16 to be supplied into the abdominal cavity AC.

Under such a gas supply state, the measured result of the first pressure sensor 95A and that of the first flow-rate sensor 96A are sent to the controller 98. The controller 98 adjusts the opening of the electropneumatic proportional valve 93 so as to regulate the pressure of the carbon dioxide gas flowing therethrough within the corresponding appropriate range of, for example, 0 to 80 mmHg or thereabout. Simultaneously, the controller 98 adjusts the opening of the electropneumatic proportional valve 93 so as to regulate the flow-rate of it within the corresponding appropriate range of, for example, 0.1 to 35 L/min or thereabout in step S26.

After a predetermined period of time has elapsed, the controller 98 sends the control signal to the first solenoid valve 94A to close it, thereby interrupting the insufflation of the carbon dioxide gas into the abdominal cavity AC (step S27), returning to step S21. Thus, the controller 98 repeatedly executes the carbon dioxide gas supply and interruption control operations for the abdominal cavity AC shown in steps S1 to S6 until the pressure measured by the first pressure sensor 95A in step S22 reaches the pressure setting set on the front panel FP or thereabout.

In contrast, when it is determined that the obtained pressure is higher than the pressure setting, that is, the determination in step S23 is YES, the controller 98 sends the first relief valve 97A to open it and keep the valve 97A opened for a predetermined period of time in step S28.

The opening of the first relief valve 97A causes carbon dioxide gas in the abdominal cavity AC to be released, thereby reducing the pressure inside the abdominal cavity AC. After the predetermined period of time has elapsed, the controller 98 sends the control signal to the first relief valve 97A to close it in step S29, and repeatedly executes the operations in step S21 to S23, S28, and S29 until the pressure inside the abdominal cavity AC falls down to the pressure setting.

On the other hand, while the abdominal cavity select button 82 is in off state, in other words, the operation mode of the controller 98 is not in the abdominal-cavity insufflation mode (the determination in step S21 is NO), the controller 98 shifts to step S30. Similarly, when the abdominal cavity pressure reaches the pressure setting or thereabout, so that the determination in step S24 is YES, the controller 98 shifts to step S30.

In step S30, the controller 98 determines whether the lumen select button 83 is turned on, in other words, its operation mode is the lumen insufflation mode.

When the lumen select button 83 is in on state, the controller 98 determines its operation mode is the lumen insufflation mode, in other words, the determination in step S30 is YES so that the controller 98 enters the lumen insufflation mode.

In the lumen insufflation mode, while the switch portion 44*a* of the foot switch 44 is in on state, the controller 98 sends the control signals to the electropneumatic proportional valve 93 and the second solenoid valve 93B, respectively. The control signal sent to the electropneumatic proportional valve 93 allows it to open by a predetermined opening and the control signal sent to the second solenoid valve 94B allows it to open. As a result, the carbon dioxide gas supplied up to the inlet of the electropneumatic proportional valve 93 to flow through the electropneumatic proportional valve 93 so that the pressure and the flow-rate of the carbon dioxide gas are regulated within the corresponding predetermined ranges suitable for the insufflation of the lumen BC, respectively. The carbon dioxide gas with its pressure and flow-rate being regulated, respectively, passes through the second solenoid valve 94B to be supplied into the lumen BC through the second adapter 41B, the lumen tube 45*b*, the adapter 43, and the gas delivery channel SC inside the flexiblescope 31.

Incidentally, because the first solenoid valve 94A is closed, no carbon dioxide gas is supplied to the first $CO_2$ supply path DC1 for the abdominal cavity AC.

Specifically, the controller 98 obtains the pressure value inside the lumen BC based on the pressure measured by the second pressure sensor 95B with the second solenoid valve 94B closed, thereby displaying the obtained pressure value on the pressure display 80*a* in step S31.

The controller 98 determines whether the obtained pressure value is higher than the pressure setting set on the front panel FP and displayed on the pressure display 80*b* (step S32).

When determining that the obtained pressure is lower than the pressure setting, that is, the determination in step S32 is NO, the controller 98 determines whether the obtained pressure value reaches the pressure setting set on the front panel FP and displayed on the pressure display 80*b* or thereabout (step S33).

When determining that the obtained pressure does not reach the pressure setting, that is, the determination in step S33 is NO, the controller 98 calculates the difference between the obtained pressure and the pressure setting to determine a pressure reduction value of the electropneumatic proportional valve 93 based on the calculated difference.

Subsequently, the controller 98 sends the control signal to the second solenoid valve 94B to open it (step S34). Next, the controller 98 sends the control signal to the electropneumatic proportional valve 93 to open it by a predetermined opening corresponding to the determined pressure reduction value.

As a result, the carbon dioxide gas, which is reduced in pressure to the predetermined pressure by the pressure reduction unit 92, is supplied into the lumen BC through the second $CO_2$ supply path DC2. Specifically, the carbon dioxide gas with the predetermined pressure is supplied through the electropneumatic proportional valve 93, the fourth flow channel C4, the second solenoid valve 94B, the seventh flow channel C7, the second flow rate sensor 96B, the eighth flow channel C8, and the second adapter 41B. Thereafter, the carbon dioxide gas with the predetermined pressure is delivered through the lumen tube 45*b*, the flexible scope 31 and the like to be supplied into the lumen BC.

Under such a gas supply state, the measured result of the second pressure sensor 95B and that of the second flow-rate sensor 96B are sent to the controller 98. The controller 98 adjusts the opening of the electropneumatic proportional valve 93 so as to regulate the pressure of the carbon dioxide gas flowing therethrough within the corresponding appropriate range of, for example, 0 to 500 mmHg or thereabout. Simultaneously, the controller 98 adjusts the opening of the electropneumatic proportional valve 93 so as to regulate the flow-rate of it within the corresponding appropriate range of, for example, 1 to 3 L/min or thereabout in step S35.

After a predetermined period of time has elapsed, the controller 98 sends the control signal to the second solenoid valve 94B to close it, thereby interrupting the insufflation of the carbon dioxide gas into the lumen BC (step S36), returning to step S21. Thus, the controller 98 repeatedly executes the carbon dioxide gas supply and interruption control operations for the lumen BC shown in steps S21, S30 to S36 until the pressure measured by the second pressure sensor 95B in step S31 reaches the pressure setting set on the front panel FP or thereabout.

In contrast, when it is determined that the obtained pressure is higher than the pressure setting, that is, the determination in step S32 is YES, the controller 98 sends the second relief valve 97B to open it and keep the valve 97B opened for a predetermined period of time in step S37.

The opening of the second relief valve 97B causes carbon dioxide gas in the lumen BC to be released, thereby reducing the intraluminal pressure of the lumen BC. After the predetermined period of time has elapsed, the controller 98 sends the control signal to the second relief valve 97B to close it in step S38, and repeatedly executes the operations in step S30 to S32, S37, and S38 until the pressure inside the lumen BC falls down to the pressure setting.

As described above, the gas supply apparatus 41 according to the second embodiment, in addition to obtaining the same effects as the first embodiment, provides the following effect. Specifically, in the second embodiment, the first relief valve 97A or the second relief valve 97B allows the pressure inside the abdominal cavity AC or that inside the lumen BC to decrease when it is higher than the corresponding one of the pressure settings.

This results in that, when the pressure inside the abdominal cavity AC or that inside the lumen BC is higher than the corresponding pressure setting, it is possible to regulate the pressure inside the abdominal cavity AC or that inside the lumen to the corresponding one of the pressure settings.

Figure 12:
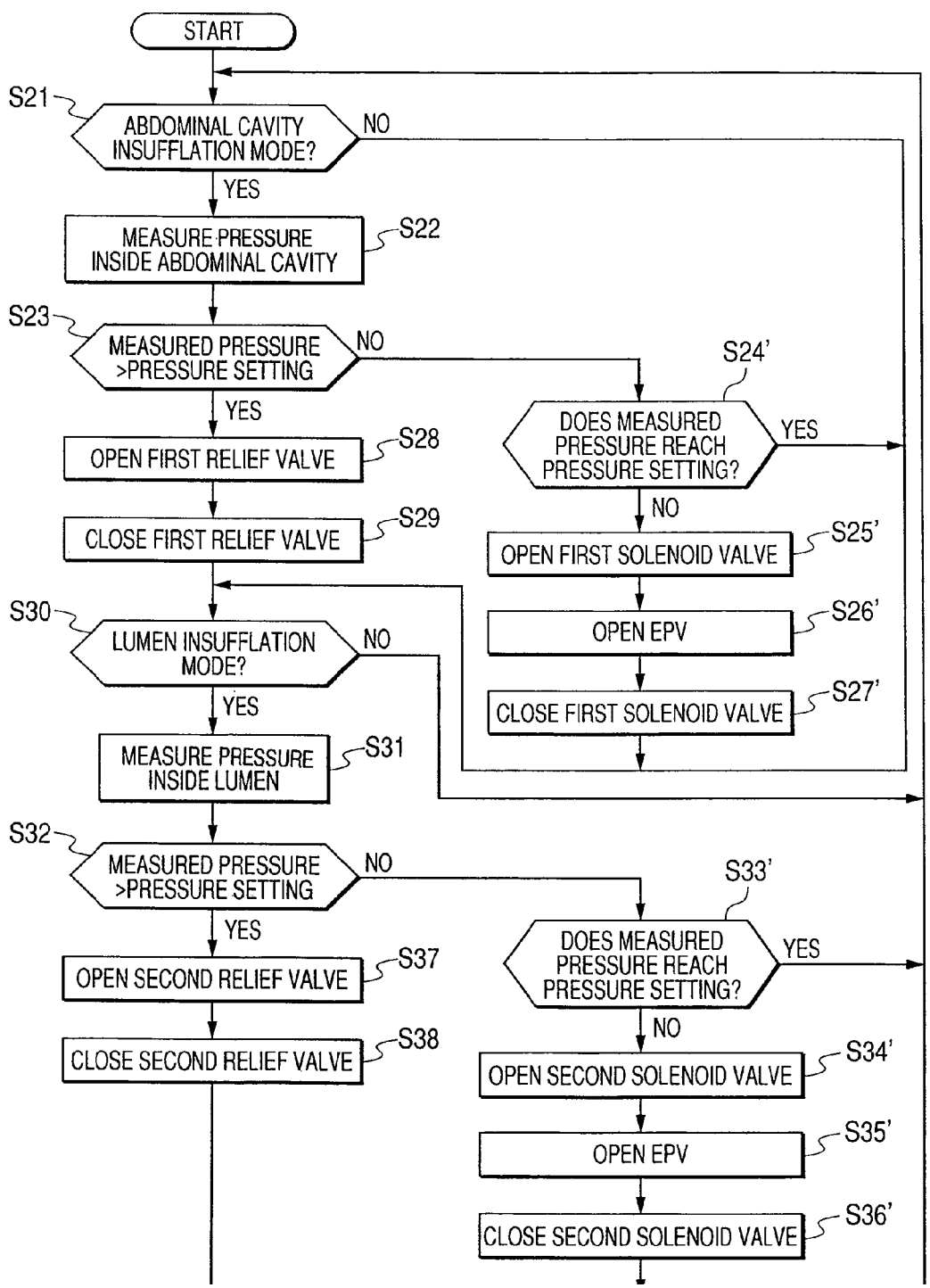
FIG. 12 is a flowchart schematically illustrating another example of control operations of a controller according to a third embodiment of the invention.

FIG. 12 represents another example of control operations of the controller 98 of the gas supply apparatus 41 according to the second embodiment.

Specifically, in the control operations shown in FIG. 11, when both the abdominal-cavity insufflation mode and the lumen insufflation mode are selected (both buttons 82 and 83 are on state), the controller 98 executes the operations in steps S25 to S27. The operations allow insufflation of the carbon dioxide gas into the abdominal cavity AC until the pressure inside the abdominal cavity AC reaches the corresponding pressure setting. After that, the controller 98 executes the operations in steps S34 to S36 to insufflate the carbon dioxide gas into the lumen BC until the intraluminal pressure of the lumen BC reaches the corresponding pressure setting.

In contrast, in the control operations shown in FIG. 12, when both the abdominal-cavity and the lumen insufflation modes are selected, the controller 98 alternately executes the insufflation control operations in steps S25' to S27' and those in steps S34' to S36' until the pressures inside the abdominal cavity AC and the lumen BC reach the corresponding pressure settings, respectively.

Specifically, the controller 98 determines whether the obtained pressure value in step S23 reaches the pressure setting or thereabout (FIG. 12; step S24'). When determining that the obtained pressure does not reach the pressure setting, that is, the determination in step S24' is NO, the controller 98, as well as the first embodiment, causes each of the first solenoid valve 94A and the electropneumatic proportional valve 93 to open, thereby supplying the carbon dioxide gas into the abdominal cavity AC.

After a predetermined period of time has elapsed, the controller 98 closes the first solenoid valve 94A in step S27'.

Subsequently, when the lumen select button 83 is in on state (determination in step S30 is YES), the controller 98 obtains the pressure value inside the lumen BC based on the pressure measured by the second pressure sensor 95B with the second solenoid valve 94B closed in step S31.

Thus, the controller 98 determines whether the obtained pressure value reaches the pressure setting set on the front panel FP and displayed on the pressure display 80b or thereabout (step S33'). When determining that the obtained pressure does not reach the pressure setting, that is, the determination in step S33' is NO, the controller 98 causes each of the second solenoid valve 94B and the electropneumatic proportional valve 93 to open, thereby supplying the carbon dioxide gas into the lumen BC The controller 98 repeatedly executes the control operations shown in steps S23, S24' to S27', S30 to S32, and S33' to S36' until the pressure inside abdominal cavity AC and that inside the lumen BC reach the corresponding pressure settings, respectively.

Incidentally, when the pressure inside the abdominal cavity AC or that inside the lumen BC is higher than the corresponding one of the pressure settings, the first relief valve 97A or the second relief valve 97B is opened to release the carbon dioxide gas in the abdominal cavity AC or in the lumen BC. This allows the pressure inside the abdominal cavity AC or that inside the lumen BC to decrease, obtaining the same effects as those in the first embodiment.

Third Embodiment

The configuration of a surgical system with a gas supply apparatus according to a third embodiment of the present invention is substantially identical to that of the surgical system 1 according to the first embodiment. Reference numerals assigned to elements of the surgical system according to the third embodiment, which are substantially identical to those of the surgical system 1, are the same as those assigned to the elements of the surgical system 1.

The third embodiment has characterized control operations of the controller 98 to reduce the pressure inside the abdominal cavity AC temporarily when a rate of pressure rise inside the lumen BC decreases, thereby making the carbon dioxide gas easily flow into the lumen BC.

The control operations of the controller 98 according to the third embodiment will be described hereinafter with reference to FIGS. 13 and 14.

Figure 13:
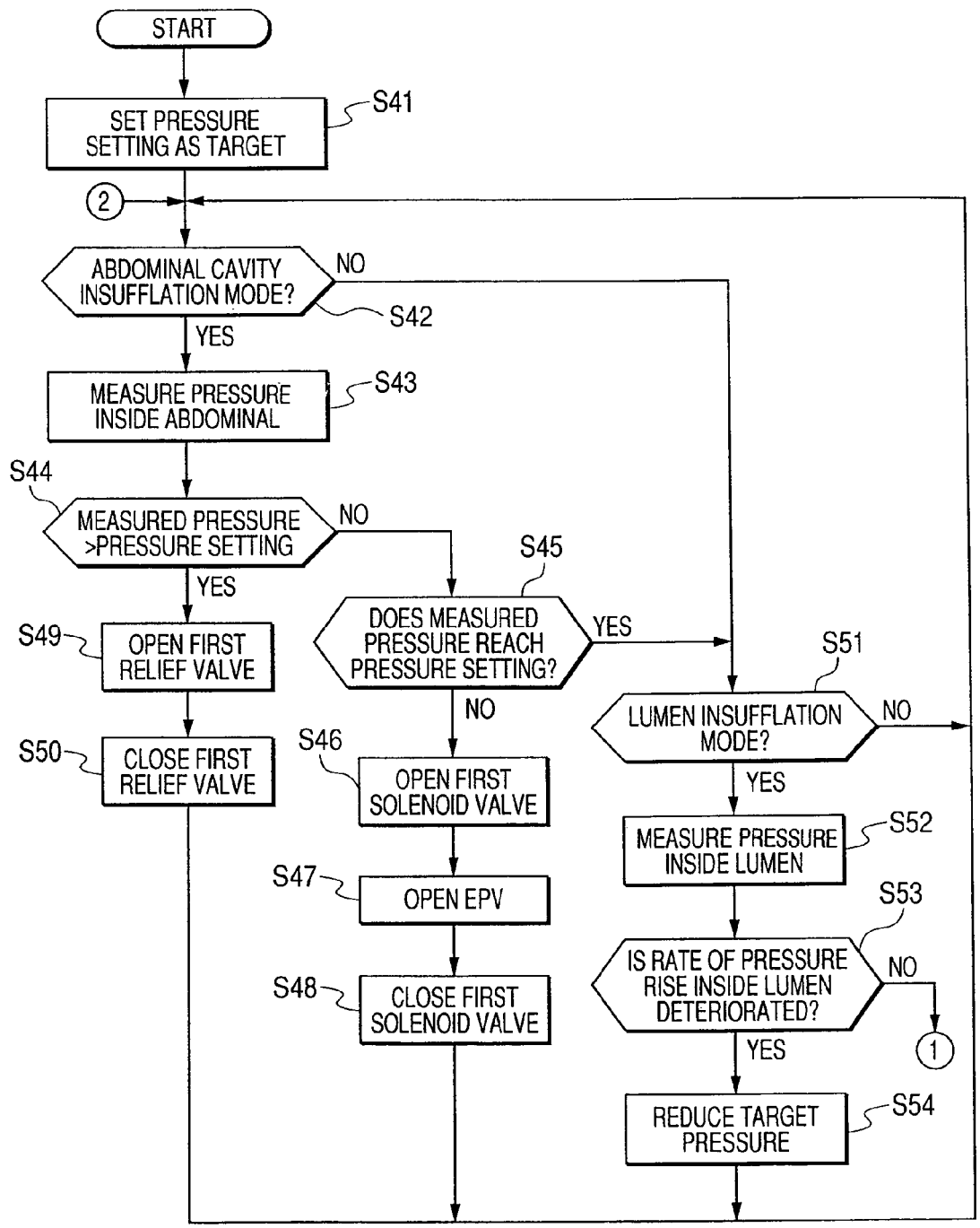
FIG. 13 is a flowchart schematically illustrating an example of control operations of a controller according to a third embodiment of the invention.
Figure 14:
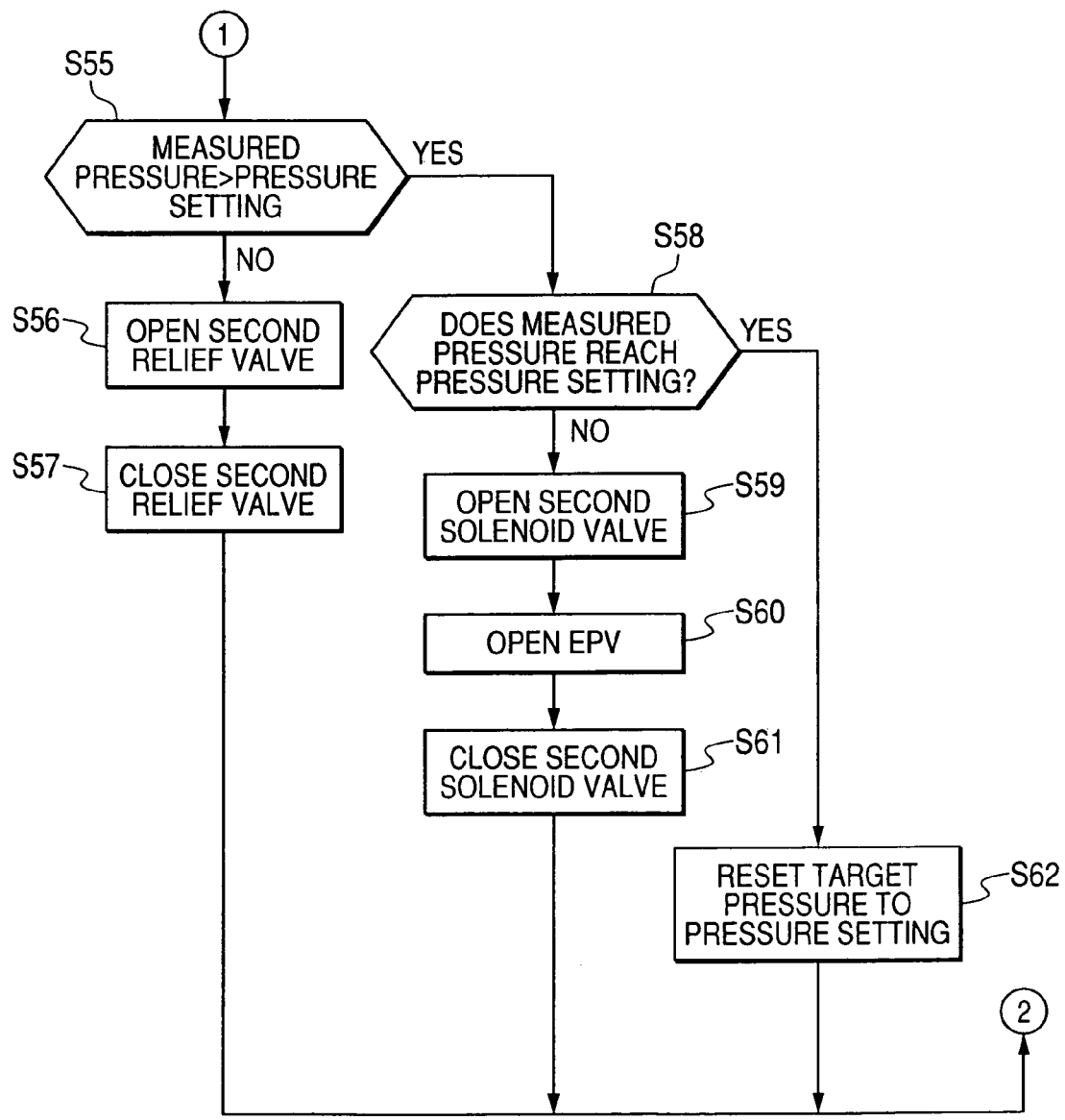
FIG. 14 is a flowchart schematically illustrating an example of control operations of the controller according to the third embodiment of the invention.

As shown in FIG. 13, the controller 98 establishes the pressure setting set on the front panel FP by the operator as a target pressure (FIG. 13; step S41). Next, the controller 98 determines whether the abdominal cavity select button 82 is turned on, in other words, its operation mode is the abdominal-cavity insufflation mode (step S42).

When the abdominal cavity select button 82 is in on state, the controller 98 determines its operation mode is the abdominal-cavity insufflation mode, in other words, the determination in step S42 is YES so that the controller 98 enters the abdominal-cavity insufflation mode.

In the abdominal-cavity insufflation mode, while the gas-supply start button 73 is in on state, the controller 98 sends the control signals to the electropneumatic proportional valve 93 and the first solenoid valve 93A, respectively. The control signal sent to the electropneumatic proportional valve 93 allows it to open by a predetermined opening and the control signal sent to the first solenoid valve 94A allows it to open. As a result, the carbon dioxide gas supplied up to the inlet of the electropneumatic proportional valve 93 to flow through the electropneumatic proportional valve 93 so that the pressure and the flow-rate of the carbon dioxide gas are regulated within the corresponding predetermined ranges suitable for the insufflation of the abdominal cavity AC, respectively. The carbon dioxide gas with its pressure and flow-rate being regulated, respectively, passes through the first solenoid valve 94A to be supplied into the abdominal cavity AC through the first adapter 41A, the abdominal cavity tube 45a, and the third trocar 16.

Incidentally, because the second solenoid valve 94B is closed, no carbon dioxide gas is supplied to the second $CO_2$ supply path DC2 for the lumen BC.

Specifically, the controller 98 obtains the pressure value inside the abdominal cavity AC based on the pressure measured by the first pressure sensor 95A with the first solenoid valve 94A closed, thereby displaying the obtained pressure value on the pressure display 77a in step S43.

The controller 98 determines whether the obtained pressure value is higher than the target pressure (step S44).

When determining that the obtained pressure is lower than the pressure setting, that is, the determination in step S44 is NO, the controller 98 determines whether the obtained pressure value reaches the target pressure (step S45).

When determining that the obtained pressure does not reach the target pressure, that is, the determination in step S45 is NO, the controller 98, as well as the first embodiment, calculates the difference between the obtained pressure and the target pressure to determine a pressure reduction value of the electropneumatic proportional valve 93 based on the calculated difference.

Subsequently, the controller 98 sends the control signal to the first solenoid valve 94A to open it (step S46). Next, the controller 98 sends the control signal to the electropneumatic proportional valve 93 to open it by a predetermined opening corresponding to the determined pressure reduction value.

As a result, the carbon dioxide gas, which is reduced in pressure to the predetermined pressure by the pressure reduction unit 92, is supplied into the abdominal cavity AC through the first $CO_2$ supply path DC1. Specifically, the carbon dioxide gas with the predetermined pressure is supplied through the electropneumatic proportional valve 93, the third flow channel C3, the first solenoid valve 94A, the fifth flow channel C5, the first flow rate sensor 96A, the sixth flow channel C6, and the first adapter 41A. Thereafter, the carbon dioxide gas with the predetermined pressure is delivered through the abdominal cavity tube 45*a* and the third trocar 16 to be supplied into the abdominal cavity AC.

Under such a gas supply state, the measured result of the first pressure sensor 95A and that of the first flow-rate sensor 96A are sent to the controller 98. The controller 98 adjusts the opening of the electropneumatic proportional valve 93 so as to regulate the pressure of the carbon dioxide gas flowing therethrough within the corresponding appropriate range of, for example, 0 to 80 mmHg or thereabout. Simultaneously, the controller 98 adjusts the opening of the electropneumatic proportional valve 93 so as to regulate the flow-rate of it within the corresponding appropriate range of, for example, 0.1 to 35 L/min or thereabout in step S47.

After a predetermined period of time has elapsed, the controller 98 sends the control signal to the first solenoid valve 94A to close it, thereby interrupting the insufflation of the carbon dioxide gas into the abdominal cavity AC (step S48), returning to step S42. Thus, the controller 98 repeatedly executes the carbon dioxide gas supply and interruption control operations for the abdominal cavity AC shown in steps S42 to S48 until the pressure measured by the first pressure sensor 95A in step S43 reaches the target pressure.

In contrast, when it is determined that the obtained pressure is higher than the target pressure, that is, the determination in step S44 is YES, the controller 98 sends the first relief valve 97A to open it and keep the valve 97A opened for a predetermined period of time in step S49.

The opening of the first relief valve 97A causes carbon dioxide gas in the abdominal cavity AC to be released, thereby reducing the pressure inside the abdominal cavity AC. After the predetermined period of time has elapsed, the controller 98 sends the control signal to the first relief valve 97A to close it in step S50, and repeatedly executes the operations in step S42 to S44, S49, and S50 until the pressure inside the abdominal cavity AC falls down to the target pressure.

On the other hand, while the abdominal cavity select button 82 is in off state, in other words, the operation mode of the controller 98 is not in the abdominal-cavity insufflation mode (the determination in step S42 is NO), the controller 98 shifts to step S51. Similarly, when the abdominal cavity pressure reaches the pressure setting or thereabout, so that the determination in step S45 is YES, the controller 98 shift to step S51.

In step S51, the controller 98 determines whether the lumen select button 83 is turned on, in other words, its operation mode is the lumen insufflation mode.

When the lumen select button 83 is in on state, the controller 98 determines its operation mode is the lumen insufflation mode, in other words, the determination in step S51 is YES so that the controller 98 enters the lumen insufflation mode.

In the lumen insufflation mode, while the switch portion 44*a* of the foot switch 44 is in on state, the controller 98 sends the control signals to the electropneumatic proportional valve 93 and the second solenoid valve 93B, respectively. The control signal sent to the electropneumatic proportional valve 93 allows it to open by a predetermined opening and the control signal sent to the second solenoid valve 94B allows it to open. As a result, the carbon dioxide gas supplied up to the inlet of the electropneumatic proportional valve 93 to flow through the electropneumatic proportional valve 93 so that the pressure and the flow-rate of the carbon dioxide gas are regulated within the corresponding predetermined ranges suitable for the insufflation of the lumen BC, respectively. The carbon dioxide gas with its pressure and flow-rate being regulated, respectively, passes through the second solenoid valve 94B to be supplied into the lumen BC through the second adapter 41B, the lumen tube 45*b*, the adapter 43, and the gas delivery channel SC inside the flexiblescope 31.

Incidentally, because the first solenoid valve 94A is closed, no carbon dioxide gas is supplied to the first $CO_2$ supply path DC1 for the abdominal cavity AC.

Specifically, the controller 98 obtains the pressure value inside the lumen BC based on the pressure measured by the second pressure sensor 95B with the second solenoid valve 94B closed, thereby displaying the obtained pressure value on the pressure display 80*a* in step S52.

The controller 98 determines whether a rate of rise of the obtained pressure value deteriorates in step S53. In other words, the rate of rise of the pressure inside the lumen BC is lower than a predetermined threshold rate in step S53.

As an example of the operation in step S53, the controller 98 calculates a rate of rise of the pressure inside the lumen BC for a predetermined period of time, which is represented as dP/dt. Where "P" indicates the pressure inside the lumen BC, and "t" indicates the predetermined period of time. Subsequently, the controller 98 compares the rate of rise "dP/dt" with the predetermined threshold rate to determine whether the rate of rise of the pressure inside the lumen BC deteriorates based on the compared result.

When it is determined that the rate of rise of the pressure inside the lumen BC deteriorates, for example, the rate of rise "dP/dt" is lower than the predetermined threshold rate, the determination in step S53 is YES. Thus, the controller 98 decreases the target pressure established by the operation in step S41 by a predetermined value (step S52), returning to step S42. Specifically, the controller 98 repeatedly executes the operations in steps S42 to S44, S49, and S50 until the pressure inside the lumen BC reaches the target pressure, which has been changed in step S54.

In contrast, when it is determined that the rate of rise of the pressure inside the lumen BC is kept sufficiently high so that it does not deteriorate, for example, the rate of rise "dP/dt" is as high as or higher than the predetermined threshold rate, the determination in step S53 is NO. Hence, the controller 98 determines whether the obtained pressure value is higher than the pressure setting set on the front panel FP and displayed on the pressure display 80b (FIG. 14; step S55).

When it is determined that the obtained pressure is higher than the pressure setting, that is, the determination in step S55 is YES, the controller 98 sends the second relief valve 97B to open it and keep the valve 97B opened for a predetermined period of time in step S56.

The opening of the second relief valve 97B causes carbon dioxide gas in the lumen BC to be released, thereby reducing the pressure inside the lumen BC. After the predetermined period of time has elapsed, the controller 98 sends the control signal to the second relief valve 97B to close it in step S57, and repeatedly executes the operations in step S51 to S57 until the pressure inside the lumen BC falls down to the pressure setting.

In contrast, when determining that the obtained pressure is lower than the pressure setting, that is, the determination in step S55 is NO, the controller 98 determines whether the obtained pressure value reaches the pressure setting set on the front panel FP and displayed on the pressure display 80b or thereabout (step S58).

When determining that the obtained pressure does not reach the pressure setting, that is, the determination in step S58 is NO, the controller 98 calculates the difference between the obtained pressure and the pressure setting to determine a pressure reduction value of the electropneumatic proportional valve 93 based on the calculated difference.

Subsequently, the controller 98 sends the control signal to the second solenoid valve 94B to open it (step S59). Next, the controller 98 sends the control signal to the electropneumatic proportional valve 93 to open it by a predetermined opening corresponding to the determined pressure reduction value.

As a result, the carbon dioxide gas, which is reduced in pressure to the predetermined pressure by the pressure reduction unit 92, is supplied into the lumen BC through the second $CO_2$ supply path DC2. Specifically, the carbon dioxide gas with the predetermined pressure is supplied through the electropneumatic proportional valve 93, the fourth flow channel C4, the second solenoid valve 94B, the seventh flow channel C7, the second flow rate sensor 96B, the eighth flow channel C8, and the second adapter 41B. Thereafter, the carbon dioxide gas with the predetermined pressure is delivered through the lumen tube 45b, the flexible scope 31 and the like to be supplied into the lumen BC.

Under such a gas supply state, the measured result of the second pressure sensor 95B and that of the second flow-rate sensor 96B are sent to the controller 98. The controller 98 adjusts the opening of the electropneumatic proportional valve 93 so as to regulate the pressure of the carbon dioxide gas flowing therethrough within the corresponding appropriate range of, for example, 0 to 500 mmHg or thereabout. Simultaneously, the controller 98 adjusts the opening of the electropneumatic proportional valve 93 so as to regulate the flow-rate of it within the corresponding appropriate range of, for example, 1 to 3 L/min or thereabout in step S60.

After a predetermined period of time has elapsed, the controller 98 sends the control signal to the second solenoid valve 94B to close it, thereby interrupting the insufflation of the carbon dioxide gas into the lumen BC (step S61), returning to step S51. Thus, the controller 98 repeatedly executes the carbon dioxide gas supply and interruption control operations for the lumen BC shown in steps S51 to S53, and S55 to S61 until the pressure measured by the second pressure sensor 95B in step S42 reaches the pressure setting set on the front panel FP or thereabout.

On the other hand, in step S58, when it is determined that the obtained pressure reaches the pressure setting, that is, the determination in step S58 is YES. In this case, when reducing the target pressure from the pressure setting established on the front panel FP and displayed on the pressure display 77b in step S54, the controller 98 resets the target pressure to the pressure setting (step S62), repeatedly executing the operations in steps S42 to S61.

Figure 15:
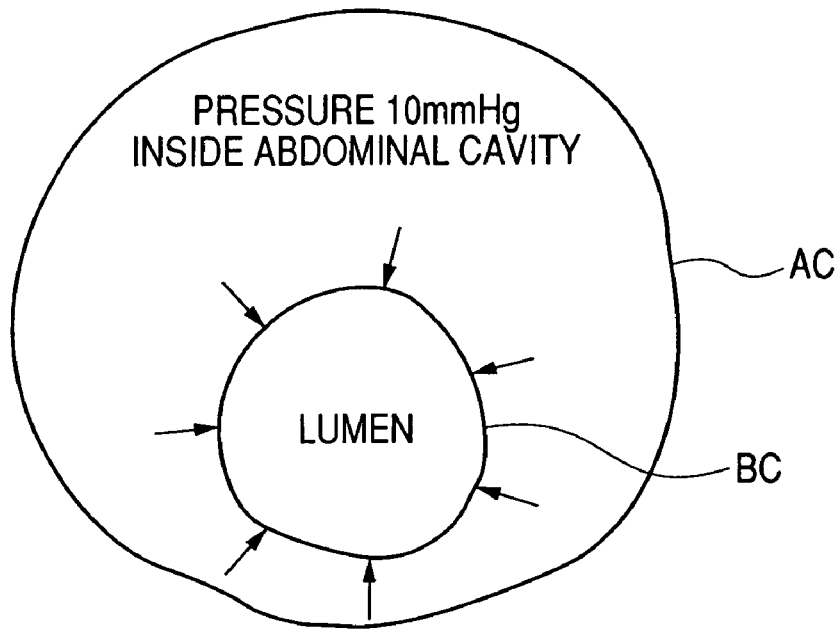
FIG. 15 is a view schematically illustrating a lumen affected by a pressure of an abdominal cavity of 10 mmHg.

In the third embodiment, in a case where the pressure setting for the abdominal cavity AC set on the front panel FP is 10 mmHg, and the pressure inside the abdominal cavity AC coincides with the pressure setting of 10 mmHg (see FIG. 15). In this case, because the lumen BC is located in the abdominal cavity AC, the pressure inside of the abdominal cavity AC exerts an influence upon the lumen BC, which prevents the carbon dioxide gas from flowing into the lumen BC.

Figure 16:
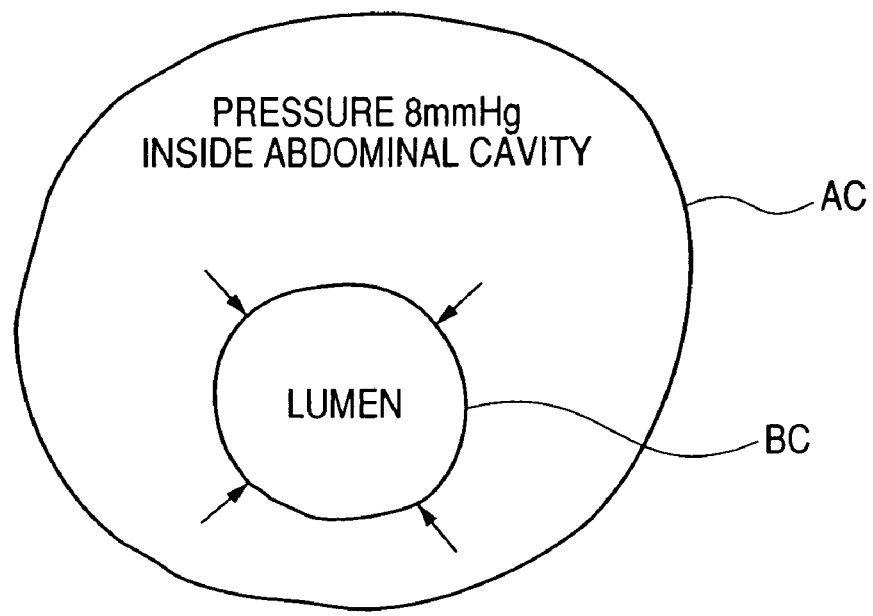
FIG. 16 is a view schematically illustrating the lumen affected by the pressure of the abdominal cavity of 8 mmHg.

On this point, in the present invention, when it is difficult for the carbon dioxide gas to flow into the lumen BC, the target pressure is reduced from 10 mmHg to 8 mmHg (see FIG. 16), and the operations in steps S51 to S53 and steps S55 to S61 are executed by the controller 98. This results in that the pressure inside the abdominal cavity AC is reduced, which lessens the influence of pressure inside the abdominal cavity on the lumen BC, thereby making the carbon dioxide gas easily flow into the lumen BC.

As set forth above, in the gas supply apparatus 41 according to the third embodiment, when the rate of pressure rise inside the lumen BC, it is possible to temporarily reduce the pressure inside the abdominal cavity AC. This allows the lumen BC to smoothly distend with the influence of the abdominal cavity's pressure lessened, making it possible to improve the operating efficiency of the laparoscopic surgery system 1.

Fourth Embodiment

The configuration of a gas supply apparatus according to a fourth embodiment of the present invention is substantially identical to that of the gas supply apparatus 41 according to the first embodiment. Reference numerals assigned to elements of the gas supply apparatus according to the fourth embodiment, which are substantially identical to those of the surgical system 1, are the same as those assigned to the elements of the gas supply apparatus 41.

Figure 17:
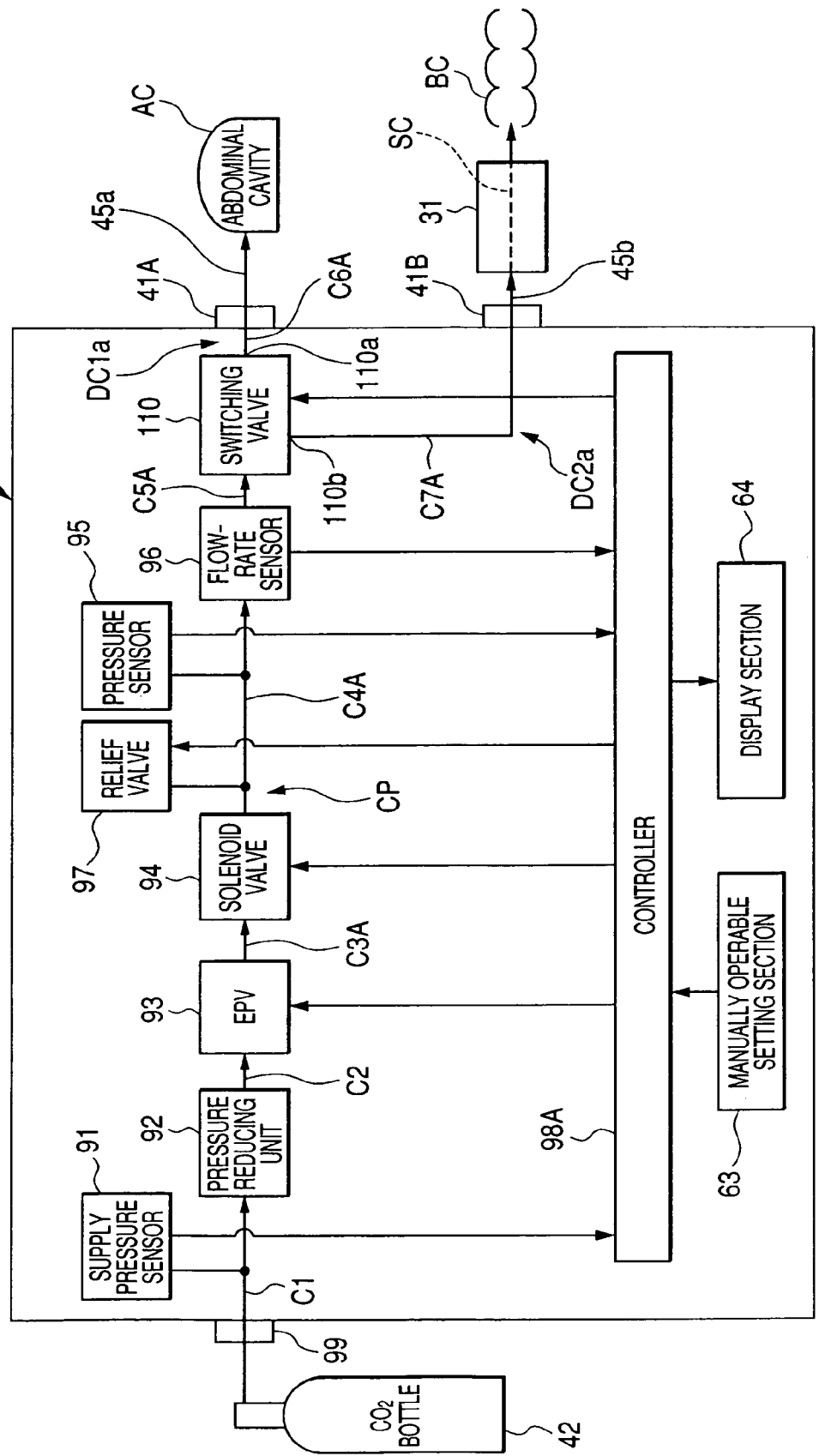
FIG. 17 is a block diagram illustrating a schematic structure of a gas supply apparatus according to a fourth embodiment of the present invention.

As shown in FIG. 17, the gas supply apparatus 41X of the fourth embodiment is provided with the high pressure adapter 99, the first delivery channel C1, the supply pressure sensor 91, and the pressure reducing unit 92 serving as, for example, a pressure regulator. The gas supply apparatus 41X includes the second delivery channel C2, the electropneumatic proportional valve (EPV) 93 as an example of pressure regulating valves, serving as the pressure regulator, a third delivery channel C3A, and a fourth delivery channel C4A.

In addition, the gas supply apparatus 41X includes an electromagnetic valve (solenoid valve) 94 as an example of open/close valves. The electromagnetic valve 94 serves as the pressure regulator.

The gas supply apparatus 41X includes a fifth delivery channel C5A, a sixth delivery channel C6A, a pressure sensor 95, a flow-rate sensor 96. Moreover, the gas supply apparatus 41A includes a seventh delivery channel C7A, a relief valve 97, a controller 98A, the manually operable setting section 63, the display section 64, and the first and second adapters 41A and 41B.

As shown in FIG. 17, because the gas supply apparatus 41X of the fourth embodiment whose elements located at the upstream of the electropneumatic proportional valve 93 are substantially identical to those of the gas supply apparatus 41 of the first embodiment, so that the descriptions of which are omitted or simplified.

As shown in FIG. 17, the gas supply apparatus 41X of the fourth embodiment is provided with a common $CO_2$ supply path CP for both the abdominal cavity AC and the lumen BC, which is coupled to the outlet of the electropneumatic proportional valve 33. The common $CO_2$ supply path CP is composed of the third delivery channel C3A, the solenoid valve 94, the fourth delivery channel C4A, the flow-rate sensor 96, and the fifth delivery channel C5A.

The solenoid valve 94 is connected to the outlet of the electropneumatic proportional valve 93 through the third delivery channel C3A. The outlet of the solenoid valve 94 is connected to the inlet of the flow-rate sensor 96 through the fourth delivery channel C4A. The pressure sensor 95 is attached to the fourth delivery channel C4A. The relief valve 97 is attached to the fourth delivery channel C4A at the upstream of the pressure sensor 95. The flow-rate sensor 96 is configured to detect a flow-rate of the carbon dioxide gas passing through the fourth delivery channel C4A.

The outlet of the flow-rate sensor 96 is connected to one end of the fifth delivery channel C5A.

In addition, the gas supply apparatus 41X is provided with a switching valve 110 whose inlet port 110c is connected to the other end of the fifth delivery channel C5A.

The switching valve 110 has two outlet ports 110a and 110b. The outlet ports 110a and 110b of the switching valve 110 are separated for the abdominal cavity AC and the lumen BC, respectively. The abdominal cavity outlet port 110a is connected to the first adapter 41A through the sixth delivery channel C6A; the lumen outlet port 110b is connected to the second adapter 42B through the seventh delivery channel C7A.

In the fourth embodiment, a first $CO_2$ supply path DC1a directing to the abdominal cavity AC includes the electropneumatic proportional valve 93, and the common $CO_2$ supply path CP constituting the third delivery channel C3A, the solenoid valve 94, the flow-rate sensor 96, and the fifth delivery channel C5A. In addition, the first $CO_2$ supply path DC1a includes the switching valve 110, the sixth delivery channel C6A, the first adapter 41A, and the abdominal cavity tube 45a. The configuration of the first $CO_2$ supply path DC1a allows the carbon dioxide gas to be introduced into the abdominal cavity AC therethrough.

In addition, in the fourth embodiment, a second $CO_2$ supply path DC2a directing to the lumen BC includes the electropneumatic proportional valve 93, and the common $CO_2$ supply path CP constituting the third delivery channel C3A, the solenoid valve 94, the flow-rate sensor 96, and the fifth delivery channel C5A. In addition, the second $CO_2$ supply path DC2a includes the switching valve 110, the seventh delivery channel C7A, the second adapter 41B, and the lumen tube 45b.

The electropneumatic proportional valve 93, the solenoid valve 94, the relief valve 97, the pressure sensor 95, the flow-rate sensor 96, and the switching valve 110 are electrically connected to the controller 98A.

The electropneumatic proportional valve 93, as well as the first embodiment, is designed to change its opening in proportional to a voltage or a current as the control signal applied from the controller 98A so as to regulate the pressure and the flow-rate of the carbon dioxide gas flowing therethrough within the corresponding appropriate ranges, respectively.

Just like the first embodiment, the solenoid valve 94 is operative to open and close based on the control signal sent from the controller 98A.

The pressure sensor 95 has a function of measuring a pressure inside the abdominal cavity AC and that inside the lumen BC, thereby sending the measured result to the controller 98A. The flow-rate sensor 96 has a function of measuring a flow-rate of the carbon dioxide gas flowing through the fourth delivery channel C4A toward the switching valve 110, thereby sending the measured result to the controller 98A.

The switching valve 110 has a function of selectively outputting the carbon dioxide gas supplied through the inlet port 110c to either the outlet port 110a or the outlet port 110b based on a control signal sent from the controller 98A.

The relief valve 97 is operative to remain in a closed state, and to open based on a control signal sent from the controller 98A.

Specifically, when the cock of the $CO_2$ bottle 42 is opened, carbon dioxide stored therein in a liquid form is vaporized to form the carbon dioxide gas. The carbon dioxide gas is delivered to the pressure reducing unit 92 through the high-pressure gas tube 46 and the like to be reduced in pressure by the pressure reducing unit 92. Thereafter, the carbon dioxide gas is delivered to the electropneumatic proportional valve 93 so that the pressure and flow-rate is regulated based on the control signals sent from the controller 98.

The carbon dioxide gas with its pressure and flow-rate regulated is delivered through the common $CO_2$ supply path CP (solenoid valve 94, the fourth delivery channel C4A, flow-rate sensor 96, and the fifth delivery channel C5A) to the switching valve 110.

The carbon dioxide gas delivered to the switching valve 110 is switched to output either the sixth delivery channel C6A or the seventh delivery channel C7A through the outlet port 110a or outlet port 110b.

Incidentally, in the fourth embodiment, a first delivery member of the present invention corresponds to, for example, at least the sixth channel C6A in the first $CO_2$ supply path DC1a, and a second delivery member thereof corresponds to, for example, at least the seventh delivery channel C7A in the second $CO_2$ supply path DC2a.

Next, operations of the gas supply apparatus 41A will be described hereinafter.

Figure 18:
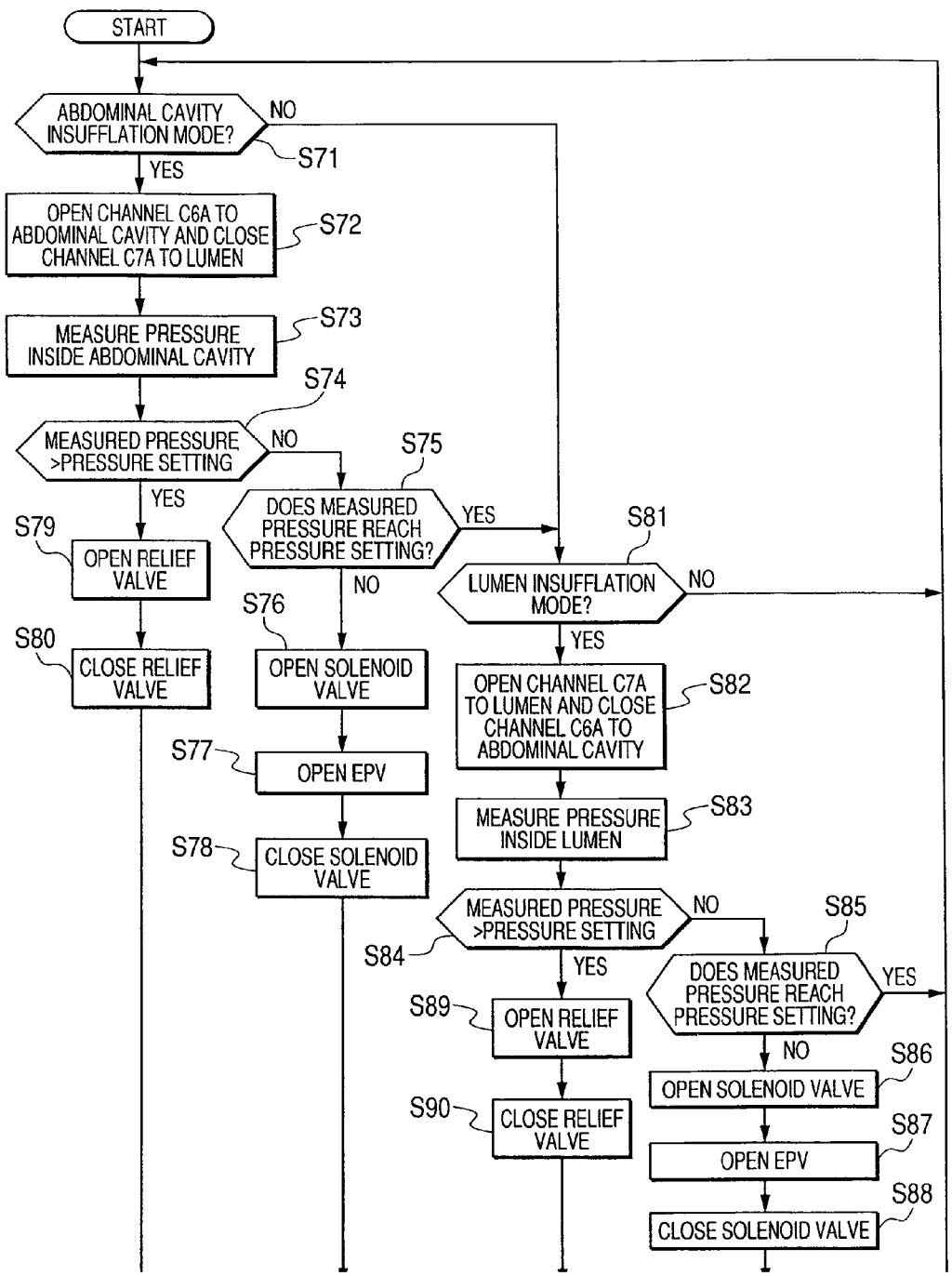
FIG. 18 is a flowchart schematically illustrating an example of control operations of a controller illustrated in FIG. 17 according to the fourth embodiment of the invention.

As shown in FIG. 18, the controller 98A determines whether the abdominal cavity select button 82 is turned on, in other words, its operation mode is the abdominal-cavity insufflation mode (FIG. 18; step S71).

When the abdominal cavity select button 82 is in on state, the controller 98A determines its operation mode is the abdominal-cavity insufflation mode, in other words, the determination in step S71 is YES so that the controller 98A enters the abdominal-cavity insufflation mode.

In the abdominal-cavity insufflation mode, while the gas-supply start button 73 is in on state, the controller 98A sends the control signal to the switching valve 110 so that the switching valve 110 switches its output to the output port 110a. Specifically, the switching valve 110 opens the sixth delivery channel C6A constituting the first $CO_2$ supply path DC1a directing to the abdominal cavity AC and closes the seventh delivery channel C7A constituting the second $CO_2$ supply path DC2a directing to the lumen BC in step S72.

That is, the switching operation of the switching valve 110 allows insufflation of the carbon dioxide gas into the abdominal cavity AC and relief therefrom.

In the abdominal-cavity insufflation mode, while the gas-supply start button 73 is in on state, the controller 98A repeatedly executes control operations shown in steps S73 to S80, which correspond to the operations shown in steps S22 to S29, respectively. These repeated operations allow the pressure inside the abdominal cavity AC to be regulated to the pressure setting established on the front panel FP.

On the other hand, while the abdominal cavity select button 82 is in off state, in other words, the operation mode of the controller 98A is not in the abdominal-cavity insufflation mode (the determination in step S71 is NO), the controller 98A shifts to step S81. Similarly, when the abdominal cavity pressure reaches the pressure setting or thereabout, so that the determination in step S75 is YES, the controller 98A shifts to step S81.

In step S81, the controller 98A determines whether the lumen select button 83 is turned on, in other words, its operation mode is the lumen insufflation mode.

When the lumen select button 83 is in on state, the controller 98A determines its operation mode is the lumen insufflation mode, in other words, the determination in step S81 is YES so that the controller 98A enters the lumen insufflation mode.

In the lumen insufflation mode, while the switch portion 44a of the foot switch 44 is in on state, the controller 98A sends the control signal to the to the switching valve 110 so that the switching valve 110 switches its output to the output port 110b. Specifically, the switching valve 110 opens the seventh delivery channel C7A constituting the second $CO_2$ supply path DC2a directing to the lumen BC and closes the sixth delivery channel C6A constituting the first $CO_2$ supply path DC1a directing to the abdominal cavity AC in step S82.

That is, the switching operation of the switching valve 110 allows insufflation of the carbon dioxide gas into the lumen BC and relief therefrom.

In the lumen insufflation mode, while the switch portion 44a of the foot switch 44 is in on state, the controller 98A repeatedly executes control operations shown in steps S81 to S90, which correspond to the operations shown in steps S30 to S38, respectively. These repeated operations allow the pressure inside the lumen BC to be regulated to the pressure setting established on the front panel FP.

As described above, in the gas supply apparatus 41X according to the fourth embodiment, providing the switching valve 110 to the upstream of the first and second adapters 41A and 41B allows commonality of the upstream $CO_2$ supply path of the switching valve 110 between the abdominal cavity AC and the lumen BC, as the common $CO_2$ supply path CP. The structure, in addition to the same effects as the second embodiment, makes it possible to reduce the number of elements of the gas supply apparatus 41X as compared with those of, for example, the gas supply apparatus 41 according to the second embodiment. For example, in the gas supply apparatus 41X according to the fourth embodiment, the number of relief valves, the number of pressure sensors, the number of flow-rate sensors, and the number of delivery channels can be reduced as compared with the gas supply apparatus 41 according to the second embodiment. As a result, it is possible to offer simplified manufacturing of the gas supply apparatus 41X and to reduce the manufacturing cost thereof.

Incidentally, in the first to fourth embodiments and their modifications, the controller 98 (98A) carries out the insufflation control operations shown in FIGS. 6, 11-14, and 17, but the system controller 5 can execute them.

In the first to fourth embodiments and their modifications, the rigidscope and the flexiblescope are used as observation devices for observing the inside of a specimen, but the present invention is not limited to the structure. Specifically, other types of endoscopes, such as a wireless capsule endoscope or the like, or other observation devices except for endoscopes, each of which is configured to be inserted into the inside of a specimen, can be used for observing the inside of the specimen.

Furthermore, it should be noted that the term "body cavity" means not only a cavity that originally exists in the body of a specimen, but also a cavity (space) to be artificially formed in the body of a specimen with medical instruments.

For example, the term "body cavity" according to the specification includes, as the former means, an abdominal cavity, a lumen including upper alimentary tracts (esophagus, stomach, or the like), lower alimentary tracts (large intestine, small intestine, or the like), a bladder, and a uterus.

In addition, the term "body cavity" according to the specification includes, as the later means, a cavity to secure the field of an endoscope during surgery, such as subcutaneous cavity and the like.

While there has been described what is at present considered to be the embodiment and modifications of the invention it will be understood that various modifications which are not described yet may be made therein, and it is intended to cover in the appended claims all such modifications as fall within the true spirit and scope of the invention.

What is claimed is:

1. A gas supply apparatus for a first body cavity and a second body cavity of a patient, the first and second body cavities being different from each other, the apparatus comprising:

a supplying unit that supplies predetermined gas;

a pressure regulator that regulates a pressure of the predetermined gas supplied from the supplying unit based on either a first pressure setting value or a second pressure setting value such that the predetermined gas with its pressure regulated based on the first pressure setting value is supplied to the first body cavity or the predetermined gas with its pressure regulated based on the second pressure setting value is supplied to the second body cavity of the patient, the first pressure setting value being suitable for an inside of the first body cavity, the second pressure setting value being suitable for an inside of the second body cavity;

a first flow adjuster that adjusts a flow of the predetermined gas regulated by the pressure regulator to the first body cavity;

a second flow adjuster that adjusts a flow of the predetermined gas regulated by the pressure regulator to the second body cavity;

a first pressure measuring unit that measures a pressure of gas inside the first body cavity;

a second pressure measuring unit that measures a pressure of gas inside the second body cavity; and a controller that:

controls the pressure regulator and the first flow adjuster based on a pressure value measured by the first pressure measuring unit to thereby match the pressure value measured by the first pressure measuring unit with the first pressure setting value, controls the pressure regulator and the second flow adjuster based on a pressure value measured by the second pressure measuring unit to thereby match the pressure value measured by the second pressure measuring unit with the second pressure setting value, calculates a rate of pressure-rise inside the second body cavity based on the pressure value measured by the second pressure measuring unit while the predetermined gas, with its pressure being regulated based on the second pressure setting value, is being supplied to the second body cavity of the patient, and reduces the first pressure setting value suitable for the inside of the first body cavity when the calculated rate of pressure-rise inside the second body cavity is lower than a preset threshold value.

2. The gas supply apparatus according to claim 1, wherein the first body cavity is an abdominal cavity inside the patient, and the second body cavity is a lumen located inside the abdominal cavity.

3. The gas supply apparatus according to claim 2, further comprising:
a relief unit for releasing the gas inside the abdominal cavity therefrom,
wherein the pressure value measured by the second pressure measuring unit changes with change in the pressure value measured by the first pressure measuring unit, and
the controller controls the relief unit to thereby release part of the gas inside the abdominal cavity therefrom based on the calculated rate of pressure-rise inside the lumen.

4. The gas supply apparatus according to claim 2, wherein the controller controls the pressure regulator, the first flow-rate adjuster, and the second flow-rate adjuster based on the pressure value measured by the first pressure measuring unit and the pressure value measured by the second pressure measuring unit such that each of the pressure values measured by the first and second pressure measuring units is kept to a corresponding one of the first and second pressure setting values.

5. The gas supply apparatus according to claim 2, wherein the pressure regulator comprises:
an electropneumatic regulator that allows the predetermined gas to be supplied to the abdominal cavity with its pressure regulated at the first pressure setting value and with its flow-rate regulated at a first flow-rate setting value, and allows the predetermined gas to be supplied to the lumen with its pressure regulated at the second pressure setting value and with its flow-rate regulated at a second flow-rate setting value.

6. The gas supply apparatus according to claim 5, wherein the controller executes:
a first control to:
cause the electropneumatic regulator to regulate the pressure of the predetermined gas at the first pressure setting value and the flow-rate thereof at the first pressure setting value;
control the second flow adjuster such that no predetermined gas flows to the lumen; and
control the first flow adjuster such that the predetermined gas with its pressure and flow-rate regulated flows to the abdominal cavity, and
a second control to:
after the pressure value measured by the first pressure measuring unit has reached the first pressure setting by the first control, cause the electropneumatic regulator to regulate the pressure of the predetermined gas at the second pressure setting value and the flow-rate thereof at the second flow-rate setting;
control the first flow adjuster such that no predetermined gas flows to the abdominal cavity; and
control the second flow adjuster such that the predetermined gas with its pressure and flow-rate regulated flows to the lumen.

7. The gas supply apparatus according to claim 5, wherein the controller:
determines whether the pressure value measured by the first pressure measuring unit is higher than the first pressure setting value;
controls the pressure regulator and the first and second flow adjusters to allow the predetermined gas to be supplied to the abdominal cavity with its pressure regulated at the first pressure setting value without the predetermined gas being supplied to the lumen when it is determined that the pressure value measured by the first pressure measuring unit is lower than the first pressure setting value;
control the relief unit to release part of the gas inside the abdominal cavity therefrom when it is determined that the pressure value measured by the first pressure measuring unit is higher than the first pressure setting value.

8. The gas supply apparatus according to claim 7, wherein the controller:
causes the first pressure measuring unit to repeatedly measure the pressure value inside the abdominal cavity;
every time the pressure value is measured by the first pressure measuring unit, determines whether the measured pressure value by the first pressure measuring unit is higher than the first pressure setting value; and
execute the control of the relief unit to release part of the gas inside the abdominal cavity therefrom until it is determined that the pressure value measured by the first measuring unit reaches the first pressure setting value.

9. The gas supply apparatus according to claim 2, further comprising:
a relief unit for releasing the gas inside the lumen therefrom,
wherein the controller:
determines whether the pressure value measured by the second pressure measuring unit is higher than the second pressure setting value;
controls the pressure regulator and the first and second flow adjusters to allow the predetermined gas to be supplied to the lumen with its pressure regulated at the second pressure setting value without the predetermined gas being supplied to the abdominal cavity;
control the relief unit to release part of the gas inside the lumen therefrom when it is determined that the pressure value measured by the second pressure measuring unit is higher than the second pressure setting value.

10. The gas supply apparatus according to claim 9, wherein the controller:
causes the second pressure measuring unit to repeatedly measure the pressure value inside the lumen;
every time the pressure value is measured by the second pressure measuring unit, determines whether the measured pressure value by the second pressure measuring unit is higher than the second pressure setting value; and
execute the control of the relief unit to release part of the gas inside the lumen therefrom until it is determined that the measured pressure value by the second pressure measuring unit reaches the second pressure setting value.

11. The gas supply apparatus according to claim 1, wherein the pressure regulator comprises:
a delivery member commonly used in the first body cavity and the second body cavity;
a pressure regulation valve coupled to the delivery member, the pressure regulation valve being configured to regulate the pressure of the predetermined gas at either the first pressure setting value or the second pressure setting value, and to supply the predetermined gas with its pressure regulated at either the first pressure setting value or the second pressure setting value to the common delivery member; and a switching unit coupled to the delivery member and the first and second body cavities, the switching unit being configured to:
switch, based on a control signal sent from the controller, output of the predetermined gas supplied through the common delivery member to the first body cavity when the pressure of the predetermined gas is regulated at the first pressure setting value; and
switch, based on the control signal sent from the controller, output of the predetermined gas supplied through the common delivery member to the second body cavity when the pressure of the predetermined gas is regulated at the second pressure setting value.

12. An observation system comprising:
a gas supply apparatus for a first body cavity and a second body cavity of a patient, the first and second body cavities being different from each other, the apparatus comprising:
a supplying unit that supplies the predetermined gas;
a pressure regulator that regulates a pressure of the predetermined gas supplied from the supplying unit based on either a first pressure setting value or a second pressure setting value such that the predetermined gas with its pressure regulated based on the first pressure setting value is supplied to the first body cavity or the predetermined gas with its pressure regulated based on the second pressure setting value is supplied to the second body cavity, the first pressure setting value being suitable for an inside of the first body cavity, the second pressure setting value being suitable for an inside of the second body cavity;
a first flow adjuster that adjusts a flow of the predetermined gas regulated by the pressure regulator to the first body cavity;
a second flow adjuster that adjusts a flow of the predetermined gas regulated by the pressure regulator to the second body cavity;
a first pressure measuring unit that measures a pressure of gas inside the first body cavity;
a second pressure measuring unit that measures a pressure of gas inside the second body cavity; and
a controller that:
controls the pressure regulator and the first flow adjuster based on a pressure value measured by the first pressure measuring unit to thereby match the pressure value measured by the first pressure measuring unit with the first pressure setting value,
controls the pressure regulator and the second flow adjuster based on a pressure value measured by the second pressure measuring unit to thereby match the pressure value measured by the second pressure measuring unit with the second pressure setting value,
calculates a rate of pressure-rise inside the second body cavity based on the pressure value measured by the second pressure measuring unit while the predetermined gas, with its pressure being regulated based on the second pressure setting value, is being supplied to the second body cavity of the patient, and
reduces the first pressure setting value suitable for the inside of the first body cavity when the calculated rate of pressure-rise inside the second body cavity is lower than a preset threshold value; and
an observation device integrated with a gas delivery channel and configured to be inserted into the second body cavity of the patient to observe the inside of the second body cavity, the gas delivery channel being coupled to the pressure regulator such that:
the predetermined gas with its pressure regulated based on the first pressure setting value by the pressure regulator is supplied to the first body cavity, or
the predetermined gas with its pressure regulated based on the second pressure setting value by the pressure regulator is supplied to the second body cavity.

13. A method of insufflating predetermined gas to a first body cavity and a second body cavity of a patient, the first and second body cavities being different from each other, the method comprising:
regulating a pressure of the predetermined gas at either a first pressure setting value or a second pressure setting value such that the predetermined gas with its pressure regulated based on the first pressure setting value is supplied to the first body cavity or the predetermined gas with its pressure regulated based on the second pressure setting value is supplied to the second body cavity of the patient, the first pressure setting value being suitable for an inside of the first body cavity, the second pressure setting value being suitable for an inside of the second body cavity;
adjusting a flow of the regulated predetermined gas to the first body cavity;
adjusting a flow of the regulated predetermined gas to the second body cavity;
measuring a pressure of gas inside the first body cavity;
measuring a pressure of gas inside the second body cavity;
matching, based on a measured pressure value of the gas inside the first body cavity, the measured pressure value of the gas inside the first body cavity with the first pressure setting value;
matching, based on a measured pressure value of the gas inside the second body cavity, the measured pressure value of the gas inside the second body cavity with the second pressure setting value;
calculates a rate of pressure-rise inside the second body cavity based on the pressure value measured by the second pressure measuring unit while the predetermined gas, with its pressure being regulated based on the second pressure setting value, is being supplied to the second body cavity of the patient, and
reducing the first pressure setting value suitable for the inside of the first body cavity when the calculated rate of pressure-rise inside the second body cavity is lower than a preset threshold value.

* * * * *